(12) United States Patent
Lakowicz

(10) Patent No.: US 7,566,783 B2
(45) Date of Patent: Jul. 28, 2009

(54) LONG WAVELENGTH LONG LIFETIME LUMINOPHORES

(76) Inventor: Joseph R Lakowicz, 10037 Fox Den Rd., Ellicott City, MD (US) 21042

( * ) Notice: Subject to any disclaimer, the term of this patent is extended or adjusted under 35 U.S.C. 154(b) by 1175 days.

(21) Appl. No.: 10/088,646

(22) PCT Filed: Jul. 23, 2001

(86) PCT No.: PCT/US01/23034

§ 371 (c)(1),
(2), (4) Date: Aug. 30, 2002

(87) PCT Pub. No.: WO02/07779

PCT Pub. Date: Jan. 31, 2002

(65) Prior Publication Data

US 2004/0039158 A1    Feb. 26, 2004

Related U.S. Application Data

(60) Provisional application No. 60/219,659, filed on Jul. 21, 2000, provisional application No. 60/246,954, filed on Nov. 9, 2000.

(51) Int. Cl.
*C09B 19/00* (2006.01)
*C07F 15/00* (2006.01)
*C07D 213/79* (2006.01)

(52) U.S. Cl. .......................... 546/10; 424/9.6; 544/64; 544/225; 546/8

(58) Field of Classification Search ................. 424/9.6; 544/64, 225; 546/8, 10
See application file for complete search history.

(56) References Cited

U.S. PATENT DOCUMENTS 5,238,808 A    8/1993    Bard et al.

*Primary Examiner*—Peter G O'Sullivan
(74) *Attorney, Agent, or Firm*—Millen, White, Zelano & Branigan, P.C.

(57) ABSTRACT

A new approach is described to making luminophores which display long emission wavelengths, long decay times, and high quantum yields. These luminophores are covalently linked or otherwise closely associated pairs with a long lifetime resonance energy transfer (RET) donor e.g., a ruthenium (Ru) metal-ligand complex, and a long wavelength acceptor, e.g., Texas Red. The donor and acceptor can be covalently linked by, e.g., poly-proline spacers. The long lifetime donor results in a long lived component in the acceptor decay which is due to RET. The quantum yield of the luminophores approaches that of the higher quantum yield acceptor, rather than the lower quantum yield typical of metal-ligand complexes. The emission maxima and decay time of such tandem luminophores can be readily adjusted by selection of the donor, acceptor and distance between them. Luminophores with these useful spectral properties can also be donor-acceptor pairs brought into close proximity by some biochemical association reaction. Luminophores with long wavelength emission and long lifetimes have numerous applications in biophysics, clinical diagnostics, DNA analysis and drug discovery.

1 Claim, 22 Drawing Sheets

D   $\underline{r=0.7\ R_0}$   A $\tau_D = 1000$ ns     $\tau_A = 1$ ns $\tau_{DA} = 100$ ns    $\tau_{AD} = 100$ ns $Q_D = 0.05$           $Q_A = 1.0$ $Q_{(D+A)} = 0.90$

TOTO-3

TO-PRO-3

LONG WAVELENGTH LONG LIFETIME LUMINOPHORES

This work was supported by NIH grant NCRR-08119 and GM 35154; the government may have rights in this invention.

BACKGROUND OF THE INVENTION

In fluorescence spectroscopy the information available from an experiment is related to the spectral properties of the fluorophore. For example, the anisotropy decay of fluorophores which display nanosecond (ns) decay times can be used to measure motions on the ns timescale. A good number of fluorophores have become available which display red or near infrared (NIR) emission [1-2]. Such probes are widely used in the biochemical and medical applications of fluorescence, including protein labeling, chromatography, measurements in blood, noninvasive medical testing, DNA sequencing and analysis and in vivo measurements [3-13]. Many of the red/NIR fluorophores display high extinction coefficients and good quantum yields, both of which indicate the absorportion and emisson electronic transitions are strongly-allowed. Consequently, the decay times of the red/NIR probes are typically below 4 ns and often below 1 ns, as is predicted by theory [14]. These fluorophores typically display small Stokes' shifts, and scattered light is most difficult to eliminate at wavelengths close to the excitation wavelength.

If slower motions on the μs timescale are of interest then it is necessary to use fluorophores which display μs decay times. Furthermore, intracellular fluorophores which require UV excitation result in a background of undesired emission due to the intrinsic fluorescence of cells and tissues. This autofluorescence from biological samples is mostly on the ns timescale and its intensity decreases at longer excitation and emission wavelengths. The signal-to-background ratio cannot be significantly improved by gated detection after the excitation pulse. Hence, the signals detected with red or NIR probes can be affected by scattered light and/or sample autofluorescence.

For these reasons, for example, there is a need for infrared fluorophores which display long excitation and long emission wavelengths and long decay times and preferably high quantum yields.

SUMMARY OF THE INVENTION

This invention relates to red/NIR luminophores which display both long decay times and high quantum yields and preferably large Stokes shifts.

In one aspect, this invention provides a method of providing a probe which emits luminophore radiation in the range of a wavelength $\lambda_1$ of about 400 nm to about 1200 nm with a high quantum yield $Q_1$ and a half life greater than about 25 ns, comprising placing a donor molecule D, which per se emits radiation of a wavelength less than $\lambda_1$ with a quantum yield substantially lower than $Q_1$, in close association with an acceptor molecule A sufficient for resonant energy transfer from D to A, as a result of which D resonantly transfers energy to A and A emits said luminophore radiation.

In another aspect this invention provides a luminophore comprising a donor portion (D) in close association with an acceptor portion (A) sufficient for resonant energy transfer from D to A, wherein upon excitation by external electromagnetic radiation of a wavelength shorter than $\lambda_1$, said luminophore emits luminophore radiation of a wavelength longer than $\lambda_1$, which is in the range of about 400 to about 1200 nm with an emission lifetime $\tau_1$ and a quantum yield $Q_1$, wherein when D is not in said close association with A, it absorbs radiation of a wavelength $\lambda_2$ shorter than $\lambda_1$ and thereafter emits radiation with a quantum yield $Q_2$ less than about 0.2, wherein when said donor portion D is in said close association with A and is excited by electromagnetic radiation of wavelength shorter than $\lambda_1$, it resonantly transfers energy to said acceptor portion A which then resonantly emits said luminophore radiation, and wherein said quantum yield $Q_1$ is substantially greater than $Q_2$.

For example, this invention provides a compound of the formula

D-L-A wherein D is a donor metal ligand complex having a quantum yield less than about 0.2 for emission in the wavelength range of greater than about 400 nm;

A is an acceptor of energy resonantly transferred from D which is then emitted in the wavelength range of about 400 to about 1200 nm; and L is a spacer of a length effective for resonant energy transfer between D and A.

In another aspect, this invention provides a chemical compound marked with a covalently bonded detectable label which is a compound above and provides the corresponding methods of labeling compounds and identifying the latter in a mixture of compounds.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein:

FIG. 11. A potential long wavelength, long lifetime luminophore based on a long lifetime donor (D) and a short lifetime acceptor (A).

Figure 1:
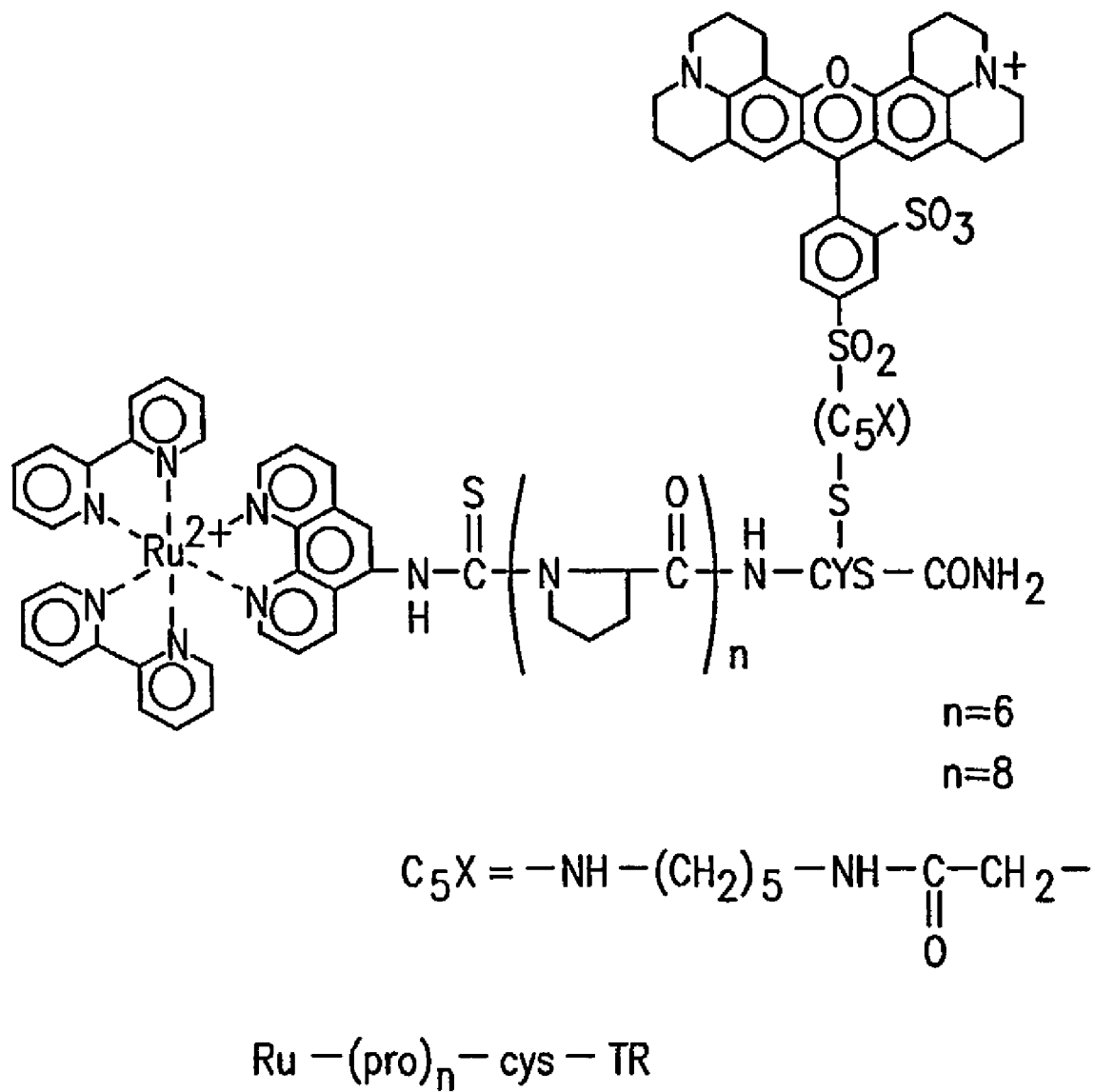
FIG. 1 shows the chemical structure of a Ru MLC covalently linked to Texas Red (D-A); wherein the donor-alone control has the sulfhydryl group blocked with iodoacetamide and the acceptor alone was the peptide without the MLC group.

Merely by way of example, the invention is illustrated by the tandem luminophore shown in FIG. 1. This luminophore displays resonance energy transfer (RET) from the exemplary ruthenium metal-ligand complex (MLC) donor shown to the exemplary Texas red (TR) acceptor. The term luminophore is used because emission from these particular MLCs display both singlet and triplet character. In no way is this term to limit this invention. A metal ligand complex is used as the donor because the transition from the triplet excited state to the singlet ground state is not allowed and these molecules display long lifetimes ranging from 100 ns to 10 µs [15-17]. Some MLCs are known which display still longer decay times from 50 to 260 µs [18-20]. Because of the long lifetimes, ease of synthesis, and range of spectral properties, the MLCs have been developed as luminescent probes in physical, analytical and biophysical chemistry [21-28].

While the MLCs display some favorable spectral properties, other properties are less favorable. For example, the MLCs display low extinction coefficients, typically less than 20,000 M$^{-1}$ cm$^{-1}$, e.g., near 10,000 M$^{-1}$ cm$^{-1}$; which is one reason for the long decay times [14], but which results in decreased sensitivity. Additionally, most MLCs display low quantum yields which rarely exceed 0.1, and the quantum yields of the MLCs with the longest decay times are often smaller [18-20]. Finally, the emission spectra are broad, which makes it more difficult to quantify the MLC emission in the presence of autofluorescence because the background is also widely distributed across the wavelength scale. Broad emission spectra also result in significant spectral overlap of the emission spectra of various MLCs, and an inability to use measurements at multiple emission wavelengths to resolve multiple species in a macroscopic or microscopic samples.

In the present invention, these limitations of the available MLC and red/NIR probes are overcome. The luminophore of this invention comprises a MLC which displays a long lifetime and low quantum yield and which is, e.g., covalently linked to a high quantum yield acceptor which typically is a short lifetime fluorophore. The luminophore is excited at a wavelength where the MLC absorbs, typically near 450 nm for the exemplary ruthenium (Ru) MLCs. The emission therefrom is red shifted to longer wavelengths by RET to the red/NIR emitting acceptor. Some long wavelength probes have low absorption near 450 nm so that most of the incident light is absorbed by the donor. Much if not most of the acceptor emission is thus due to energy transfer from the MLC.

Following pulsed excitation, the excited state population of the MLC becomes the only excitation source for the acceptor, which continues to emit as long as MLCs remain in the excited state. Such luminophores can still display long decay times in the presence of RET. For instance, if the MLC donor displays a lifetime of 1 µs in the absence of RET, the lifetime of the luminophore is expected to decrease to 100 ns if the RET efficiency is 90%, e.g., D-A distance being 0.7 Ro (Förster distance). A decay time of 100 ns is much longer than can be obtained with known red/NIR probes and 100 ns is longer than most autofluorescence. With a 10 µs decay time donor, 90% transfer efficiency will result in a 1 µs component in the acceptor decay.

Assuming that the acceptor does not absorb at the donor excitation wavelength ($\lambda_D^{ex}$), the acceptor is excited solely by RET from the donor. Since the acceptor lifetime is short ($\tau_D$=1 ns), the acceptor intensity will closely follow the donor intensity. Hence the acceptor will display the same decay time as the donor and the acceptor decay time ($\tau_{AD}$) will be near 100 ns. Most acceptors will display some absorption at the donor excitation wavelength. In this case the acceptor emission will typically display two decay times, a ns component due to directly excited acceptor, and long decay time near 100 ns due to RET from the donor. The long lifetime emission acceptor can be readily isolated with gated detection, which is readily accomplished with photo multiplier tubes (PMTs) [78-80]. Gated detection is frequently used in immunoassay based on the lanthanides [81, 82].

Figure 12:
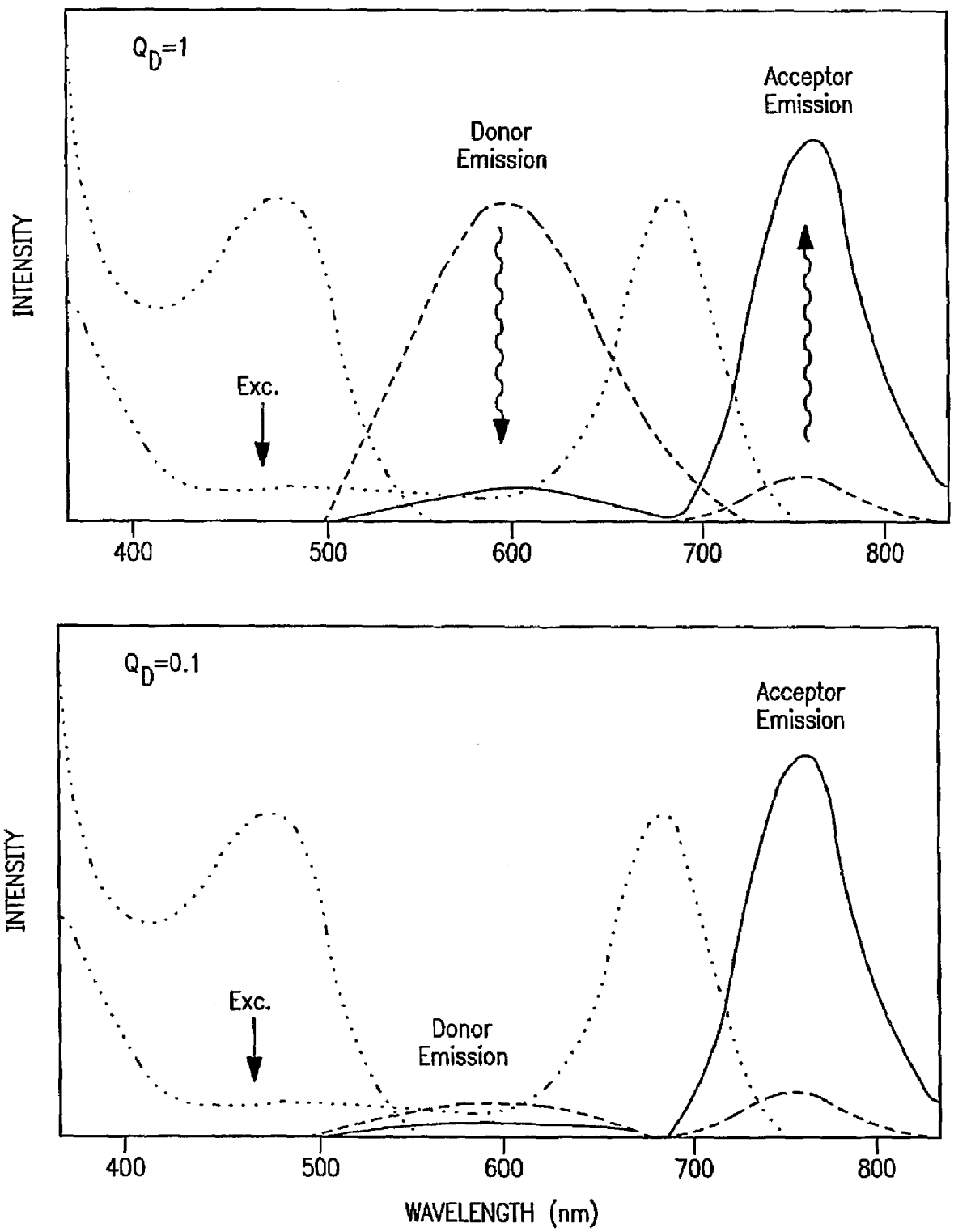
FIG. 12. Intuitive description of resonance energy transfer from a high quantum yield donor ($Q_D$=1.0, top) and a low quantum yield donor ($Q_D$=0.1, bottom). For both panels $\epsilon_A/\epsilon_D$=0.1. For the low quantum yield donor RET results in an increase in the overall quantum efficiency of the tandem luminophore.

An important advantage of such a RET probe (FIG. 11) is an increase in the effective quantum yield of the long lifetime luminophore. This effect is illustrated in FIG. 12. Suppose the donor and acceptor both display quantum yields of unity ($Q_D=Q_A=1.0$). In this case (top) RET quenches the donor and results in an equivalent increase in the emission intensity of the acceptor. The integrated or total intensity of the donor and acceptor remains the same in the presence or absence of RET.

A surprisingly different result is obtained if the donor displays a low quantum yield. For example, the commonly used ruthenium MLCs have quantum yields of 0.05 or less. In this case the donor emission without RET is much weaker (FIG. 12, lower panel). However, RET to a nearby acceptor still results in the same increased intensity of the acceptor. More specifically, the transfer efficiency can approach unity even though the donor quantum yield is low. A favorable result of efficient RET from the donor is that the wavelength integrated intensity of the D-A pair can be almost 20-fold larger than that of the donor or acceptor alone. More specifically, for 100% transfer efficiency, the overall quantum yield becomes the quantum yield of the acceptor. These considerations suggest that tandem RET probes based on MLC donors can be used to create long lifetime probes, with red-NIR emission, with the added advantage of an increased effective quantum yield. Additionally, the modular design of these probes allows practical and rational adjustment of the spectra properties including the excitation and emission wavelengths and the decay times.

Luminophores of this invention are typified in FIG. 11, which shows a long lifetime donor (D) which is covalently linked to an acceptor (A), with spectral properties such that resonance energy transfer occurs with moderate to high efficiency. In this case the D-to-A distance is assumed to be 0.7 $R_0$, where $R_0$ is the Förster distance,. This separation results in approximately 90% transfer. The donor is preferably a luminescent transition metal-ligand complex (MLC). Many such MLCs are known, and they can display a wide range of absorption and emission wavelengths and long decay times ranging from 100 ns to 10 μs [15-16]. In recent years these complexes have been developed for use as luminescent probes [21, 22] for studies of protein dynamics, immunoassays and chemical sensing [23-28].

The theory and application of RET have been described in numerous reviews [31-33]. (The following discussion of theory is in no way intended to be limiting.) Discussed here are those aspects of RET needed to demonstrate the occurrence of a RET enhanced quantum yield and the appearance of a long lifetime component in the acceptor decay. The rate of energy transfer for a donor to an acceptor is given by $$k_T = \frac{1}{\tau_D^0}\left(\frac{R_0}{r}\right)^6 \quad (1)$$

where $\tau_D^0$ is the donor lifetime in the absence of acceptor, r is the donor-to-acceptor distance, and $R_0$ is the Förster distance at which RET is 50% efficient. The value of $R_0$ can be accurately calculated from the spectral properties of the donor and acceptor.

Figure 2:
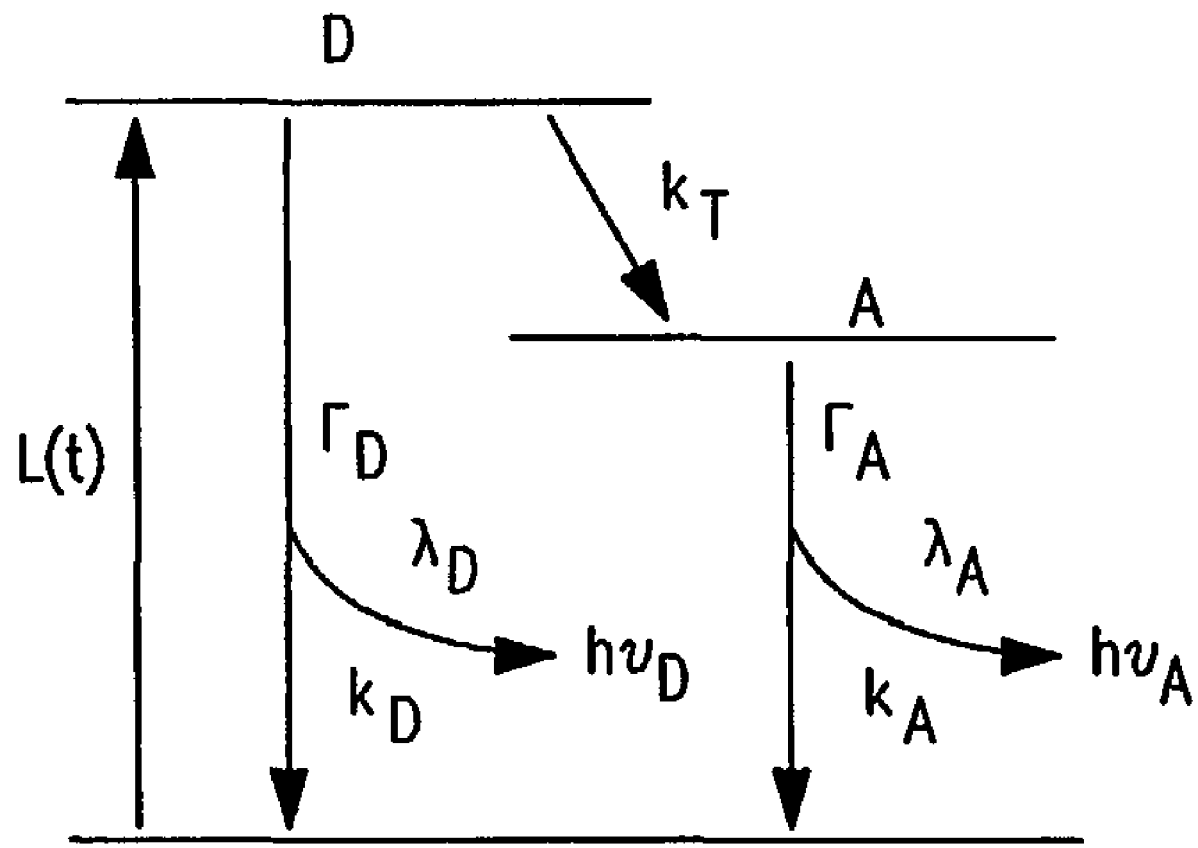
FIG. 2 shows a Jablonski diagram for an irreversible excited state process.

Consider the donor-acceptor pair FIG. 1. Assume the donor has a lifetime $\tau_D^0=1$ μs and the acceptor a lifetime of $\tau_A^0=1$ ns when directly excited. The efficiency of energy transfer is given by the ratio of the transfer rate to the total rate of donor deactivation, which is the reciprocal of the lifetime. Hence the transfer efficiency (E) from the donor is given by $$E = \frac{k_T}{k_T+\Gamma_D} = \frac{k_T}{\lambda_D+k_D+k_T} \quad (2)$$

where $\Gamma_D=(\tau_D^0)^{-1}=(\lambda_D+k_D)^{-1}$ is the decay rate of the donor in the absence of acceptor, and $\lambda_D$ and $k_D$ are the radiative and non-radiative decay rates, respectively (FIG. 2). The transfer efficiency (E) can be determined experimentally from the relative intensities of the donor in the absence ($F_D$) and presence ($F_{DA}$) of acceptor $$E = 1 - \frac{F_{DA}}{F_D} \quad (3)$$

The transfer efficiency can also be determined from the donor decay times in the absence ($\tau_D^0$) or presence ($\tau_D$) of acceptors $$E = 1 - \frac{\tau_D}{\tau_D^0} \quad (4)$$

This expression is only valid when the donor decay is a single exponential. The decay time of the donor in the presence of acceptor is given by $$\tau_D=1/(k_T+\Gamma_D) \quad (5)$$

which is the reciprocal of the sum of the deactivation rates of the donor.

The possibility of using rapid RET to improve the system quantum yield with low quantum yield donors can be seen from the equations which describe the donor ($F_D$) or acceptor ($F_A$) intensities. In the kinetic scheme of FIG. 2, the intensity of the donor and acceptor is proportional to the amount of light absorbed or the extinction coefficient ($\epsilon_D$ and $\epsilon_A$) and the fraction of the absorbed light which is emitted. Hence in the absence of RET $$F_D^\circ = \frac{\lambda_D \varepsilon_D}{\lambda_D+k_D} = Q_D^0\varepsilon_D = \tau_D^0\lambda_D\varepsilon_D \quad (6)$$

$$F_A^\circ = \frac{\lambda_A \varepsilon_A}{\lambda_A+k_A} = Q_A^0\varepsilon_A = \tau_A^0\lambda_A\varepsilon_A \quad (7)$$

where $\epsilon_A$ and $\epsilon_D$ are the extinction coefficients at the wavelength used to excite the donor. The lifetimes of the unquenched donor and the directly excited acceptor are given by $(\tau_D^0)^{-1}=\lambda_D+k_D$ and $(\tau_A^0)^{-1}=\lambda_A+k_A$. The quantum yields of the donors or acceptors in the absence of energy transfer are given by the ratio of the emissive rates ($\lambda_D$ or $\lambda_A$) to the sum of the rate process which depopulates the excited state ($\lambda_D+k_D$) or ($\lambda_A+k_A$). There is usually some acceptor emission even in the absence of RET due to direct absorption (excitation) of the acceptor resulting from the non-zero value of $\epsilon_A$. For clarity the proportionality constant is dropped which should be on the right side of each equations 6 and 7.

In the absence of RET the total intensity ($F_T^o$) of the donor ($F_D^o$) and acceptor ($F_A^o$) is that due to direct excitation of both species $$F_T^o = F_D^o + F_A^o = \frac{\lambda_D \varepsilon_D}{\lambda_D + k_D} + \frac{\lambda_A \varepsilon_A}{\lambda_A + k_A} = Q_D^0 \varepsilon_D + Q_A^0 \varepsilon_A \quad (8)$$

where $F_T^o$ is the total emission in the absence of transfer. Now assume RET occurs with a rate $k_T$. The intensities of the donor and acceptor are given by $$F_D = \frac{\lambda_D \varepsilon_D}{\lambda_D + k_D + k_T} = Q_D \varepsilon_D \quad (9)$$

$$F_A = \frac{\lambda_A \varepsilon_A}{\lambda_A + k_A} + \frac{k_T \varepsilon_D}{\lambda_D + k_D + k_T} \cdot \frac{\lambda_A}{\lambda_A + k_A} \quad (10)$$

The intensity or quantum yield of the donor $Q_D = \lambda_D/(\lambda_D + k_D + k_T)$ is decreased by an additional rate $k_T$ which depopulates the donor (eq. 9). The intensity of the acceptor is increased by the transfer rate $k_T$. The transfer efficiency term $E = k_T/(\lambda_D + k_D + k_T)$ in eq. 10 can be understood as the fraction of absorbed photons absorbed by the donor which are transferred to the acceptor. These transferred photons are emitted with a quantum yield $Q_A = \lambda_A/(\lambda_A + k_A)$. The energy received from the donor is emitted with the quantum yield of the acceptor. The combined emission intensity of the donor and acceptor is given by $$F_T = F_D + F_A = Q_D \varepsilon_D + Q_A^o(\varepsilon_A + E\varepsilon_D) = Q_D^o \varepsilon_D (1-E) + Q_A^o (\varepsilon_A + E\varepsilon_D) \quad (11)$$

It is instructive to consider the limits of very slow ($k_T \to 0$ and $E \to 0$) and very fast ($k_T \to \infty$) energy transfer. In the limit of no energy transfer the total intensity becomes equal to that of a mixture of two non-interacting fluorophores (eq. 8). In the limit of rapid transfer ($k_T \to \infty$ and $E \to 1$) the total intensity becomes $$F_T = \frac{\lambda_A (\varepsilon_A + \varepsilon_D)}{\lambda_A + k_A} = Q_A (\varepsilon_A + \varepsilon_D) \quad (12)$$

This is an important result which indicates the total intensity is proportional to the sum of the extinction coefficients and to the quantum yield of the acceptor. This occurs because the energy transfer can occur with an efficiency of one even if the donor quantum yield is low. If the rate of energy transfer is fast and if the acceptor absorbs weakly the excitation wavelength ($\varepsilon_A << \varepsilon_D$) then $$F_T = \frac{\lambda_A \varepsilon_D}{\lambda_A + k_A} = Q_A \varepsilon_D \quad (13)$$

This equation shows that with rapid energy transfer and no directly excited acceptor the acceptor emission intensity is proportional to the amount of light absorbed by the donor and the quantum yield of the acceptor. The donor-acceptor pair becomes essential to a new fluorophore with an extinction coefficient $E_D$ and a quantum yield $Q_A$.

It is informative to consider the time-dependent decays of the donor, acceptor and the total emission. These expressions are similar to those known for an excited state reaction [34-37]. Here, the reverse transfer rate from A to D is zero (FIG. 2). Additionally, since both donor and acceptor are present all times, there is some direct excitation of the acceptor in addition to the acceptor which is excited by RET from the donor. The time-dependent changes in the donor and acceptor populations are given by $$\frac{d[D]}{dt} = -(\Gamma_D + k_T)[D] + \varepsilon_D L(t) \quad (14)$$

$$\frac{d[A]}{dt} = -\Gamma_A [A] + k_T [D] + \varepsilon_A L(t) \quad (15)$$

where L(t) is the excitation function. The square brackets are taken to indicate the excited state population of each species. The time-dependent decays of the donor and acceptor are given by $$I_o(t) = N_D^0 \exp[-\Gamma_D + K_T)t] \quad (16)$$

$$I_A(t) = A \exp[-\Gamma_D + k_T)t] - (N_A^o - A) \exp[\Gamma_A t] \quad (17)$$

where $N_D^0$ and $N_A^0$ are the number of excited donors and acceptor molecules at t=0. The pre-exponential factors in eqs. 16 and 17 are proportional to $\varepsilon_D L(t)$ and $\varepsilon_A L(t)$, respectively, but not shown. The factor A $$A = \frac{N_D^0 k_T}{\Gamma_A - \Gamma_D - k_T} = \frac{-N_D^0 k_T}{\Gamma_D - \Gamma_A + k_T} \quad (18)$$

depends on the efficiency by which the acceptor is pumped by the donor. According to equation 16, the donor decay $I_A(t)$ is the usual decay rate of a donor with a transfer rate $k_T$. The acceptor decay contains a component with the lifetime of the acceptor $\tau_A \to 0$ and a component with the lifetime of the quenched donor $\tau_D$.

Suppose the acceptor decay is very rapid, that is, the directly excited acceptor displays a short lifetime, $\tau_A \to 0$ or $\Gamma_A$ is very large. Then the acceptor decay becomes $$I_A(t) = A \exp[-(\Gamma_A + k_T)t]. \quad (19)$$

This result shows that in the limit of a short acceptor lifetime the acceptor emission resulting from energy transfer displays the same lifetime as the quenched donor. A similar result is shown if one assumes $\tau_D >> \tau_A$ or $\Gamma_A >> \Gamma_D$. In this case the rightmost term in equation 17 decays rapidly to zero, relative to the donor decay, and the acceptor decay resulting from RET displays the same decay time as the donor. If there are no initially excited acceptors, $N_A^0 = 0$, equal and opposite pre-exponential factors are obtained and the acceptor decays according to $$I_A(t) = A \exp[-(\Gamma_D + k_T)t] - A \exp[\Gamma_A t] \quad (20)$$

Moreover, the inventor's publication, Lakowicz et al., Analytical Biochemistry 288, 62-75 (2001) is entirely incorporated by reference herein.

In one aspect, this invention thus involves the increase of the effective quantum yield of a luminophore by rapid RET in long lifetime MLC components having low quantum yields. Such an increase in effective quantum yield has not previously been important in the biochemical uses of RET [29-30 and 38-46] because most organic donors have good quantum yields. The increased effective quantum yield of the donor has not been important for RET with, e.g., the lanthanides because transfer from the organic chelates to the lanthanides is efficient, and the shielded lanthanide donors often display quantum yields near unity [42-46]. (See also the enhancement of lanthanide emission when bound to essential non-luminescent DNA or nucleotides [47-49]). There are numerous primary reports and review articles on RET, and the concept of using the acceptor emission to measure the transfer efficiency is not new [38-41]. Additionally, Selvin and co-workers have already noted the usefulness of measuring the long lifetime acceptor emission with lanthanide donors to selectively detect D-A pairs [42] and to provide a long decay time for the acceptor [43, 44]. Donors and acceptors with short decay times have been covalently linked for use in DNA sequencing [30, and Ju et al. PNAS, USA, 92, 4347 (1995)] and as high affinity dyes which bind non-covalently to DNA [45, 46].

The approach of this invention to tandem luminophores can be rationally and routinely used to obtain the desired spectral properties. RET is a highly predictable phenomena. The long acceptor decay time can be increased by a longer spacer. Less spectral overlap of the D and A can be obtained using shorter wavelength rhenium MLC donors or longer wavelength acceptors.

These tandem luminophores can be prepared in conjugatable forms and used as a single reagent. This invention can also be applied to the measurement of protein or DNA association reactions where the donor and acceptor are present in separate molecules and are placed in close association by the interactions of the separate molecules.

The luminophores of this invention can be used as labels fully analogous to prior art labels, e.g., those discussed in the references cited herein, e.g., by conventional covalent linking to desired molecules to be detected, e.g., nucleic acid proteins, cells, etc., probes based thereon etc.

Thus, this invention involves donor molecules/portions, D, typically having low quantum-yields less than about 0.2 or even lower, e.g., about 0.1 or about 0.01-0.2, 0.1-0.2, etc. Such donor molecules are well known. Typically they are metal ligand complexes, of transition metals (e.g., atomic numbers 21-30, 39-48 and 72-80); those of the lanthanides (e.g. atomic numbers 57-71, 81-83) are also possible, but these typically have high quantum yields. A wide variety of well known donor-type metal ligand complexes are well known. See references 15-27. See, as well, Demas et al., Coordination Chemistry Reviews 211 (2001) 317-351; Stufkens et al., Coordination Chemistry Reviews 177 (1998) 127-179. Typically, but not in a limiting way, these are of the di-imine e.g., bipyridyl type. Most preferred are the transition metal complexes, especially those of renium, ruthenium, osmium and iridium. Such D molecules are well known as having low quantum yields and having broad emission spectra at relatively long wavelengths, as mentioned above. Their emission life times are also relatively long as also mentioned above.

The acceptor molecules/portions are also per se well known in the field. Typically, these are dye molecules such as Texas Red. Albumin 633 or 670, CY5, fluorescein dyes, polymethine dyes, cyanine dyes, squarilium dyes, croconium dyes, merocyanine dyes, oxonol dyes, and many others. See e.g., WO 98/22146; and topics in Fluorescence Spectroscopy, Vol. 4: Probe Design and Chemical Sensing, ed. Joseph R. Lakowicz, Plenum Press, N.Y., 1994, Chapter 6, R. B. Thompson, pp. 151-182, and Chapter 7, Guillermo A. Casay, et al., pp. 183-222. These acceptor molecules are known as having high quantum yields per se and as emitting in relatively long wavelength regions with long lived decay times.

This invention provides a combination of molecules or closely associated component species involving both D and A molecules/portions e.g., covalently linked to one another or in close association with each other such that the spacing of the two molecules, in all cases, is effective for resonant energy transfer from the donor to the acceptor. This may be achieved not only by covalent linking but also by use of conventional biological association reactions, e.g., nucleic acid hybridization between two nucleic acid molecules (DNA, RNA, etc.), one bonded to the donor and the other bonded to the acceptor. Such association can also be achieved by other similar specifically interacting molecules, e.g., protein/nucleic acid, antibody/antigen, receptor/ligand, etc. Details of the linking of the donor and/or acceptor molecules/portions to any such molecules are fully conventional.

Where a D/A molecule is to be employed, the D portion is linked to the A portion by a spacer or linker molecule, L. The nature of the spacer is non-critical, the effective parameter being the distance between D and A and the covalently linked combination. Thus, any of the well known spacer molecules can be employed, e.g., polyalkylene moieties, polyamino acid moieties (e.g., polyproline moieties of the examples), maleimido moieties, isothiocyanate moieties, esters, ethers, secondary and tertiary amines, amides, the structures cited below, etc.

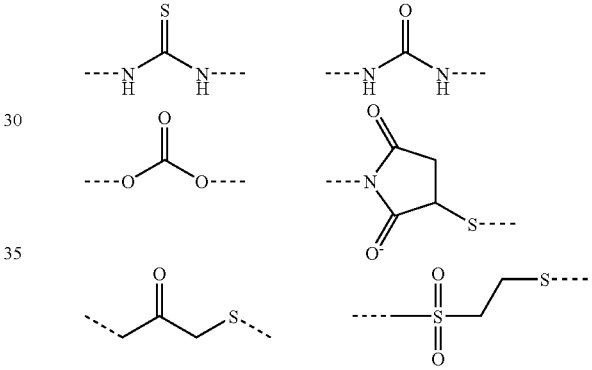

See any of the well known prior art linker-related disclosures in this regard. In general, the closer D and A are spaced from each other the faster and more efficient will be the resonant energy transfer, e.g., as can be seen from the examples. Determination of an optimal distance and a corresponding spacer is fully routine as can be seen from the literature cited herein. Typically, spacings are desired which will achieve transfer efficiencies about 10%-90%, e.g., 20-80%, 30-70%, 40-60%, efficiencies around 50% typically being satisfactory. If the transfer efficiency is too high, then the decay times achieved will be too short.

As can be seen, by routine selection of the D-moiety, A-moiety and spacer distance, "designer" probes can be achieved in accordance with this invention. See, e.g., Stufkens et al., above, e.g., pp.171-174; Chen et al., J. Am. Chem. Soc. 2000, 122, 657-660. Typically, the resultant long wavelength emission will be in the range of 400-1200 nm, e.g., 450-1200, 550-1000 nm and more typically 600-900 nm. Decay life times (half lives) will typically be greater than 25 ns, typically 25 ns-100 µ, more typically 50 ns-10 µs, and most typically 50 ns-2 µs. Luminophores of this invention having a desired emission wavelength and lifetime can be prepared in accordance with well known considerations and the guidance provided by this specification. Selection of the A and D moieties appropriate for a desired emission wavelength range can be made using conventional considerations e.g., as discussed in references 15-27, e.g., by suitable routine selection of metal and ligand combinations. Modification of the spacing length between D and A will similarly routinely be achievable by appropriate selection of chemical linking moieties, to achieve a resultant desired transfer efficiency and life time.

The production of the D and A compounds according to the invention can be carried out by conventional modification of the substances, which contain functionalities that can be coupled (e.g., carboxyl, amino, and hydroxyl groups), according to processes well known to one skilled in the art.

The production of the adducts according to the invention is carried out by reaction of the dye with a metal ligand complex or ligand complex (followed by metallation) according to methods that are well known in the literature. The dyes and complexes must have reactive groups that can be coupled in this regard or they must routinely be activated in-situ or in advance by generation of these groups. With regard, e.g., to amino- and sulfhydryl groups suitable reactive groups are, for example, N-hydroxysuccinimidylester, N-hydroxy-succinimidylester-3-sulfate, isothiocyanates, isocyanates, maleimide-, haloacetyl, vinylsulfone groups. The coupling is preferably carried out in an aqueous medium. In this case, the degree of concentration can be routinely controlled by stoichiometry and reaction time. See e.g., Snyth. Commun. 23 (1993) 3078-94, DE-OS 3912046, Cancer Immunol. Immunother. 41 (1995) 257-263, Cancer Research 54 (1994) 2643-49.

Thus, as can be seen, this invention provides luminiphor probes emitting long wavelength radiation with high quantum yield despite the involvement of absorbing donors having low quantum yields. As a result, emitter probes are provided at wavelengths to which skin is at least translucent, in which wavelength ranges background autofluorescence and natural fluorophore emissions are minimized. Such long lifetime emission is achieved also despite the use of acceptor portions (dyes) per se having short life times. This represents another significant advantage since extant background fluorescence tends to be of significantly shorter lifetimes than that achieved by the emitters of this invention.

The closely associated D/A pairs of this invention can be used straightforwardly in any of the usual probe-based techniques mentioned herein, e.g., including nucleic acid sequencing, hybridization assays, immunoassays, etc. This aspect is fully conventional. See e.g., Ota et al., Nucleic Acid Research, 1998, Vol. 26, No. 3, 735-743; Peterson et at., J. Am-Chem. Soc., 2000, 122, 7837-7838; Paris et al. Nucleic Acid Research, 1998, Vol. 29, No. 16, 3789-3793; Templeton et al., Clin. Chem. 37/9, 1506-1512 (1991); Weissleder et al., Nature Biotechnology Vol. 17, April 1999, 375-378; Xiav et al., Proc. Natl. Acad Sci., 95,15309-15314, December 1998.

Another application of this invention is for the study of macromolecular association reactions, such as protein-protein interactions, DNA hybridization [58-60], fluorescence in-situ hybridization (FISH) [61], or the use of molecular beacons [62, 63]. As an example, suppose it was necessary to test for binding of donor-labeled oligonucleotides to a mixture of acceptor-labeled oligonucleotides. When using a RuMLC donor and one of the acceptors used in this report, most of the species labeled with donor or acceptor alone will display little emission. In contrast the D-A pairs due to macromolecular association will be brightly fluorescent. Additionally, the acceptor emission will be long lived. Using time-gated detection brightly fluorescent spots may become apparent against background of weakly stained chromatin and/or short decay time. These spectral properties will be useful for detection of oligonucleotide hybridization on DNA arrays [64-65]. Such arrays are becoming widely used for analysis of gene expression [66-68].

Thus, a generic approach to obtaining an unusual combination of spectral properties by using an appropriate D-A pairs is provided. This approach can be used to create D-A pairs which acts as a single luminophore, or this effect can be used to detect interactions in samples containing species labeled with the donor or acceptor. This approach will also be useful in studies of macromolecular folding as illustrated by the use of RET to study ribozyme structures [69, 70]. One can also provide long lifetime donors linked to pH, $Ca^{2+}$, or other analyte-sensitive fluorophores [71, 72]. If the analyte sensitive fluorophore displays distinct emission spectra with and without bound analyte, then there will be a long lived component in the emission with the spectral characteristics of each form. Finally, the use of the enhanced emission, and inhibition of the enhancement, can be used in macromolecular binding assays in high throughput screening [73, 74]. There appear to be numerous applications of our approach in biochemical and biomedical research.

ABBREVIATIONS

| | |
|---|---|
| A | acceptor |
| D | donor |
| D-A | donor-acceptor pair |
| MLC | metal-ligand complexes |
| NIR | near infrared |
| PMT | photomultiplier tube |
| TR | Texas Red |
| bpy | 2,2'-bipyridine |
| phen | 1,10-phenanthroline |
| RET | resonance energy transfer |
| Ru | Ru(bpy)$_2$(phen-ITC) which has been covalently linked to a peptide or DNA oligomer |

In the foregoing and in the following examples, all temperatures are set forth uncorrected in degrees Celsius; and, unless otherwise indicated, all parts and percentages are by weight.

The entire disclosures of all applications, patents and publications, cited above and below are hereby incorporated by reference.

EXAMPLE 1

Simulations were performed to predict the spectral properties of the D-A pair for typical decay times and quantum yields. For these simulations, eq. 11 was modified to use the normalized extinction coefficient $\epsilon'_D$ and $\epsilon'_A$
where $$Q_T = Q_D^0 \epsilon'_D (1-E) + Q_A^0 (\epsilon'_A + E\epsilon'_D) \quad (21)$$

$$\epsilon'_D = \epsilon_D/(\epsilon_D + \epsilon_A) \quad (22)$$

and $$\epsilon'_A = \epsilon_A/(\epsilon_D + \epsilon_A) \quad (23)$$

Figure 3:
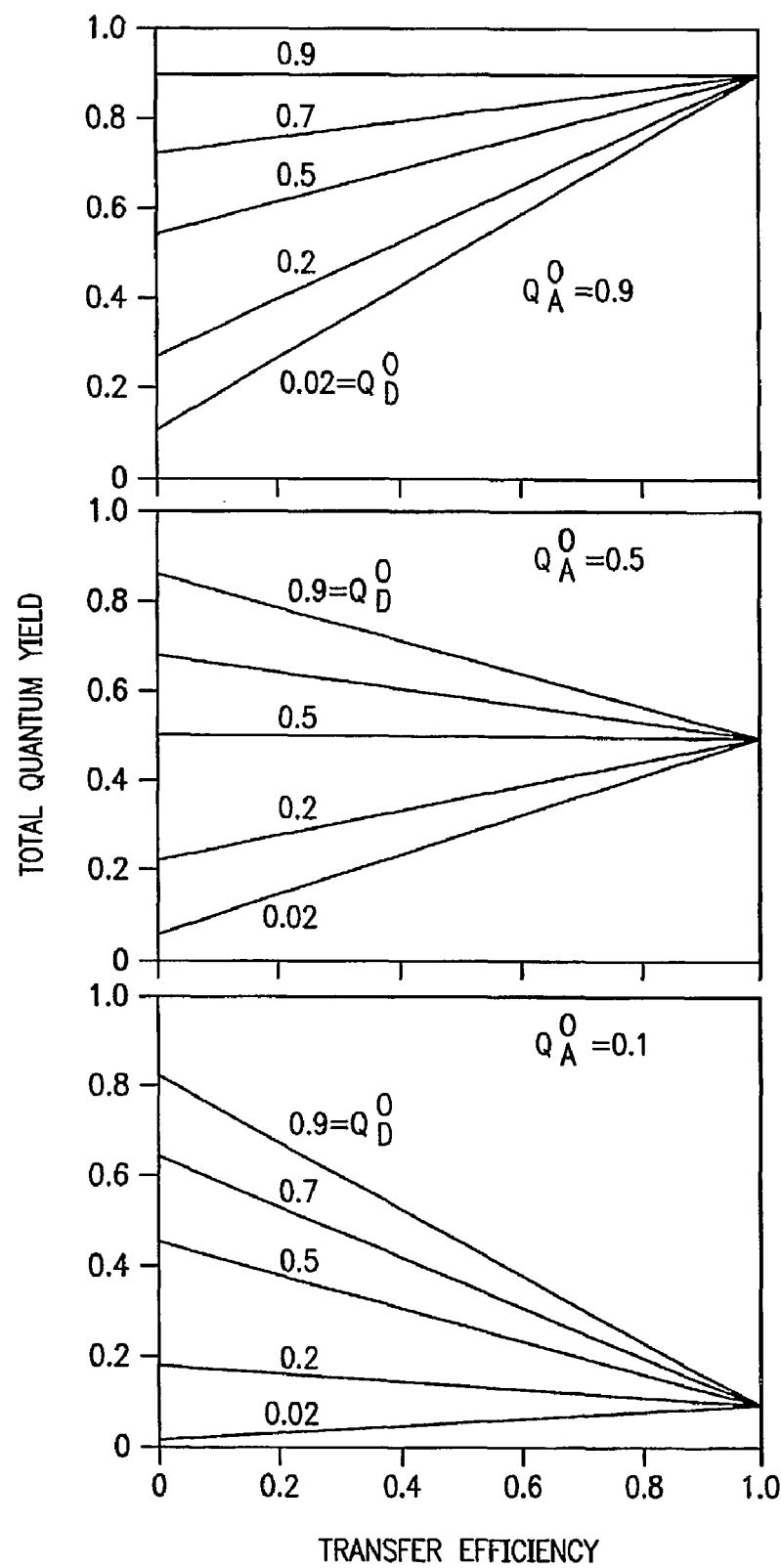
FIG. 3 shows the effect of energy transfer efficiency on the total quantum yield.

FIG. 3 shows the total quantum yield expected for three D-A pairs for various transfer efficiencies. The quantum yield of the acceptor was assumed to be high $Q_A^0 = 0.9$ (top), intermediate $Q_A^0 = 0.5$ (middle) and low $Q_A^0 = 0.1$ (lower panel). Since most acceptors will absorb at the donor excitation wavelength, we assumed the normalized extinction coefficient of the acceptor was $\epsilon'_A = \epsilon_A/(\epsilon_A + \epsilon_D) = 0.10$. As the transfer efficiency increases the total quantum yield approaches that of the acceptor. If the acceptor quantum yield is low (lower panel), then energy transfer decreases the overall quantum yield. Importantly, if the quantum yield of the acceptor is high (upper panel), the overall quantum yield approaches that of the acceptor for high transfer efficiency.

Figure 4:
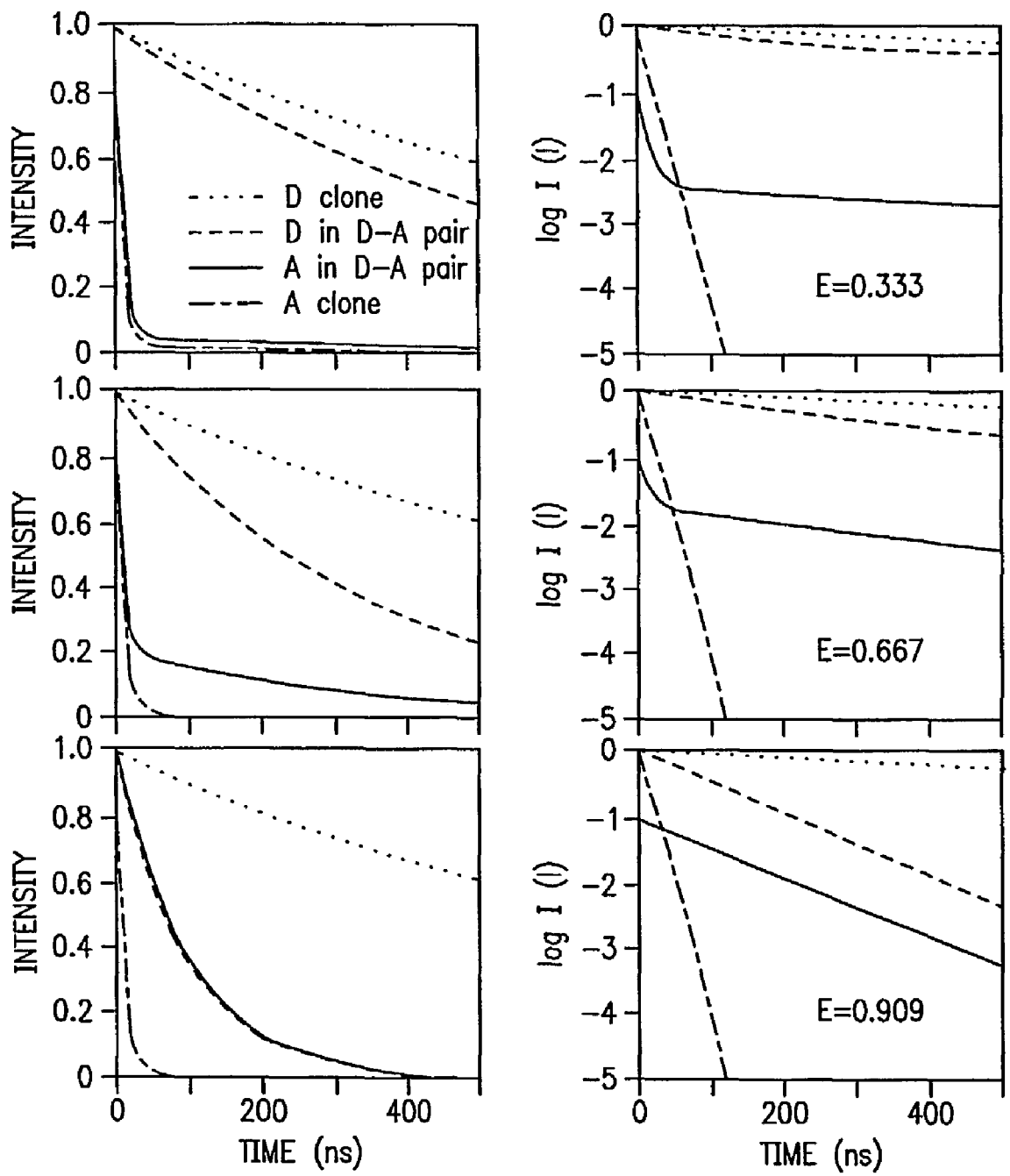
FIG. 4 shows the simulated time-dependent decays of the donor and acceptor, each alone and in a D-A pair; for these simulations $\tau_D^0$=1000 ns and $\tau_A^0$=10 ns.

The intensity decays expected for the donor and acceptor in D-A pairs for various transfer efficiencies (FIG. 4) were also simulated. The assumed decay times were $\tau_D^0$=1000 ns and $\tau_A^0$=10 ns. An important conclusion from these simulations is that the acceptor can display long decay times. If the transfer efficiency is 33% (FIG. 4, top panel), the acceptor shows a decay time with $\tau$=667 ns (Table I). The transfer efficiency can be as high as 90.9% and the acceptor still display a 91 ns decay time. Thus, usefully long decay times can be obtained even with high transfer efficiency.

EXAMPLE 2

The practical usefulness of the tandem luminophores of this invention were demonstrated using the covalently linked D-A pairs shown in FIG. 1. These D-A pairs can be considered to be the probe or reagent, in the same manner that linked DNA pairs have been developed for DNA sequencing [29-30]. Alternatively, this unique long lifetime high quantum yield emission can be the result of protein or nucleic acid association reactions.

The Texas Red iodoacetamide with a C5 linker was purchased from Molecular Probes, Inc. The [Ru(bpy)$_2$ (amino phenanthroline)]$^{2+}$ was a gift from Dr. Jonathan Dattelbaum. It was converted into isothiocyanate by treating with 500 µl of thiophosgene in 1 ml acetone for 3 hrs. Both the solvent and thiophosgene were removed under a stream of nitrogen and the isothiocynate was used immediately.

The oligo proline peptides with a cysteine at C-terminus were synthesized at the biopolymer facility of University of Maryland School of Medicine, Baltimore. The crude peptide was purified by RP-HPLC on a C18 column using a 0.1% TFA and 100% acetonitrole containing 0.05% TFA. The molecular weights were confirmed by mass spectroscopy.

The peptides were labeled first with the acceptor. Typically a mM solution of the peptide in 0.2 M bicarbonate buffer, pH 8.5, was reacted with a 2-fold excess iodoacetamide for 6 hours. The resulting peptide was purified from the free probe using a column of Sephadex G-15 running in 20% DMF solution. The labeled peptide was further purified by HPLC.

To prepare the double labeled peptide the acceptor labeled peptide was further reacted with a five-fold excess Ru isothiocynate in 0.2 M bicarbonate, pH 9.0 for 6 hours. The peptide was separated from the free probe by passing through a Sephadex G-15 column and further purified on HPLC. To prepare the donor-only peptide, the sulphydryl group was first blocked with a five-fold excess iodoacetic acid at pH 8.5 for 1 hr and to same reaction mixture a five-fold excess of the isothiocyanate was added, the pH was adjusted to 9 and allowed to react for 6 hours. The free dye was separated on a Sephadex G-15 column and the donor-labeled peptide was purified by HPLC. The purified peptides were lyophilized and stored as water solutions at 4° C.

The steady-state measurements were done in an aqueous 5 mM hepes, 100 mM NaCl, pH 8. The measurements in propylene glycol were without buffer with the propylene glycol at least 98%, the remainder being water. For the steady-state measurements the peptide concentrations were less than 2 µM and about 10 µM for the time-resolved measurements. An aqueous solution of rhodamine B with a lifetime of 1.68 ns was used as the reference. The frequency-domain lifetime measurements were done on a SLM instrument with a LED emitting at 450 nm as a light source. The emission was observed through a 630/40 nm bandpass filter.

Figure 5:
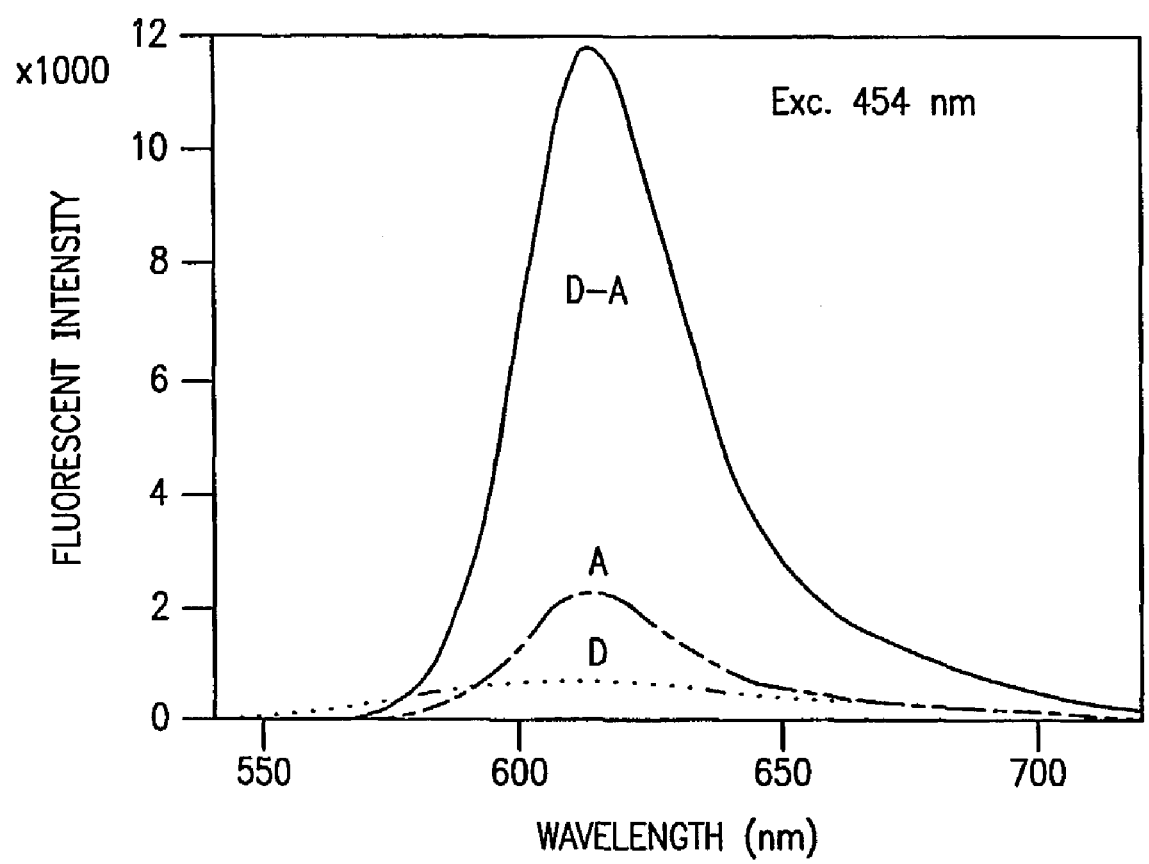
FIG. 5 shows the emission spectra of the Ru-(pro)$_6$ donor (D) the TR acceptor (A) and the covalently linked pair (D-A) in aqueous buffer.

The emission spectra of Ru-(pro)$_6$-cys-TR (FIG. 1), referred to as the (pro)$_6$ D-A pair was examined. As a control for the donor-alone (D), the structure shown in FIG. 1 was used with the sulfhydryl group blocked with iodoacetamide. For the acceptor (A), the structure shown in FIG. 1 was used without the covalently linked donors. Emission spectra of these three compounds are shown in FIG. 5. These spectra were obtained using the same molar concentrations of D, A and D-A. The overall intensity of the D-A pair is about 5-fold larger than the sum of the donor and acceptor alone. This result demonstrates that a tandem luminophore with a low quantum yield donor can display a higher quantum yield than either species alone.

Figure 6:
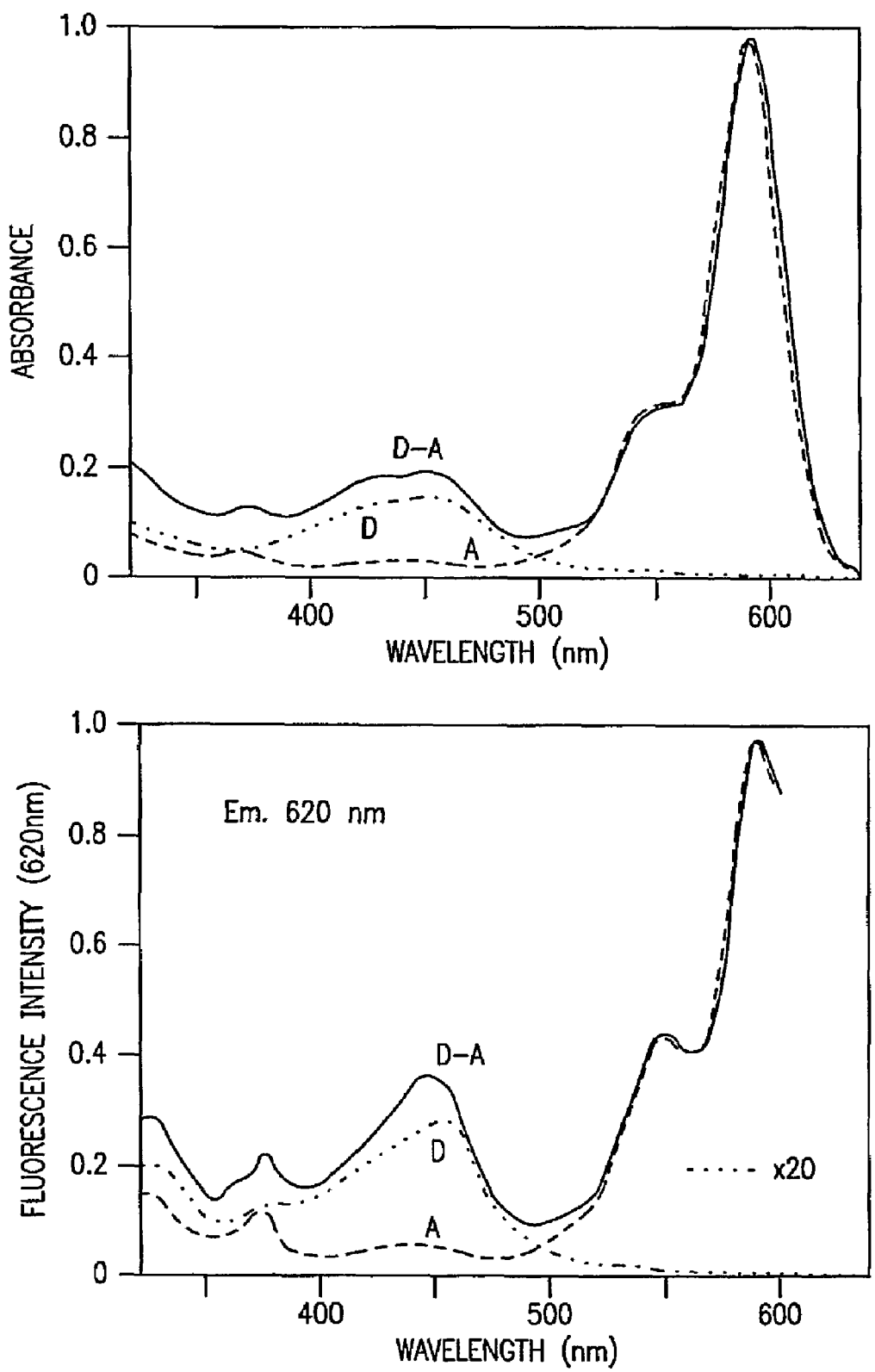
FIG. 6 shows the absorption (top) and excitation spectra (bottom) of Ru-pro)$_6$(D), TR(A), and Ru-(pro)$_6$-TR(D-A) in aqueous buffer.

FIG. 6 shows the absorption and excitation spectra of D, A and D-A. The absorption spectra of D-A was found to be essentially identical to the sum of the D-alone and A-alone absorption spectra (top). Contrasting results were found for the excitation spectra (FIG. 6, bottom). In this case the intensity of the long wavelength emission with excitation at 450 nm is about 6-fold greater than that of the directly excited acceptor and about 20-fold larger than the donor alone. This result also demonstrates the role of energy transfer in increasing the effective quantum yield of the donor.

Figure 7:
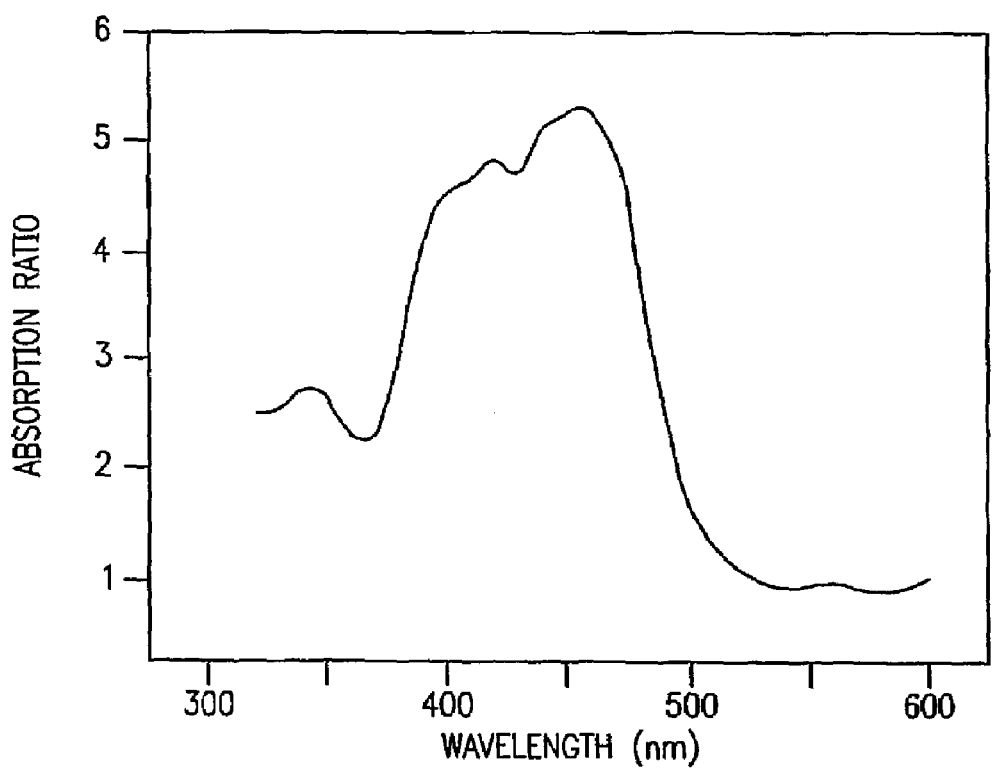
FIG. 7 shows the ratio of the absorption spectra (top) and emission spectra (bottom) of the D-A pair divided by that of the acceptor in aqueous buffer.
Figure 7:
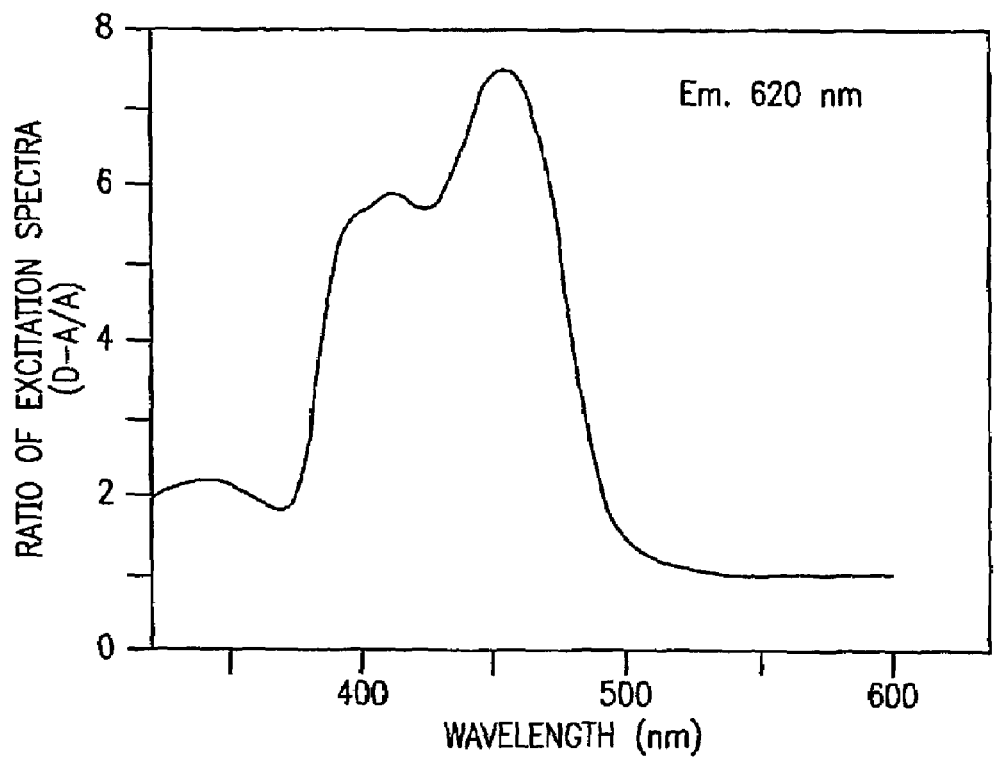

The enhanced emission demonstrated in FIGS. 5 and 6 is determined by the relative extinction coefficients of the donor and acceptor at the excitation wavelength. The ratio of the donor to the absorption spectra is shown in the top panel of FIG. 7. This ratio displays a maximum near 6 at 450 nm, which is near the peak of the donor absorption and the minimum of the acceptor absorption. The ratio of the excitation spectra shows the same trend, with a maximum near 450 nm (FIG. 7, bottom). These results demonstrate that the enhancement at the acceptor emission is determined by the ratio of the light absorbed by each species.

Figure 8:
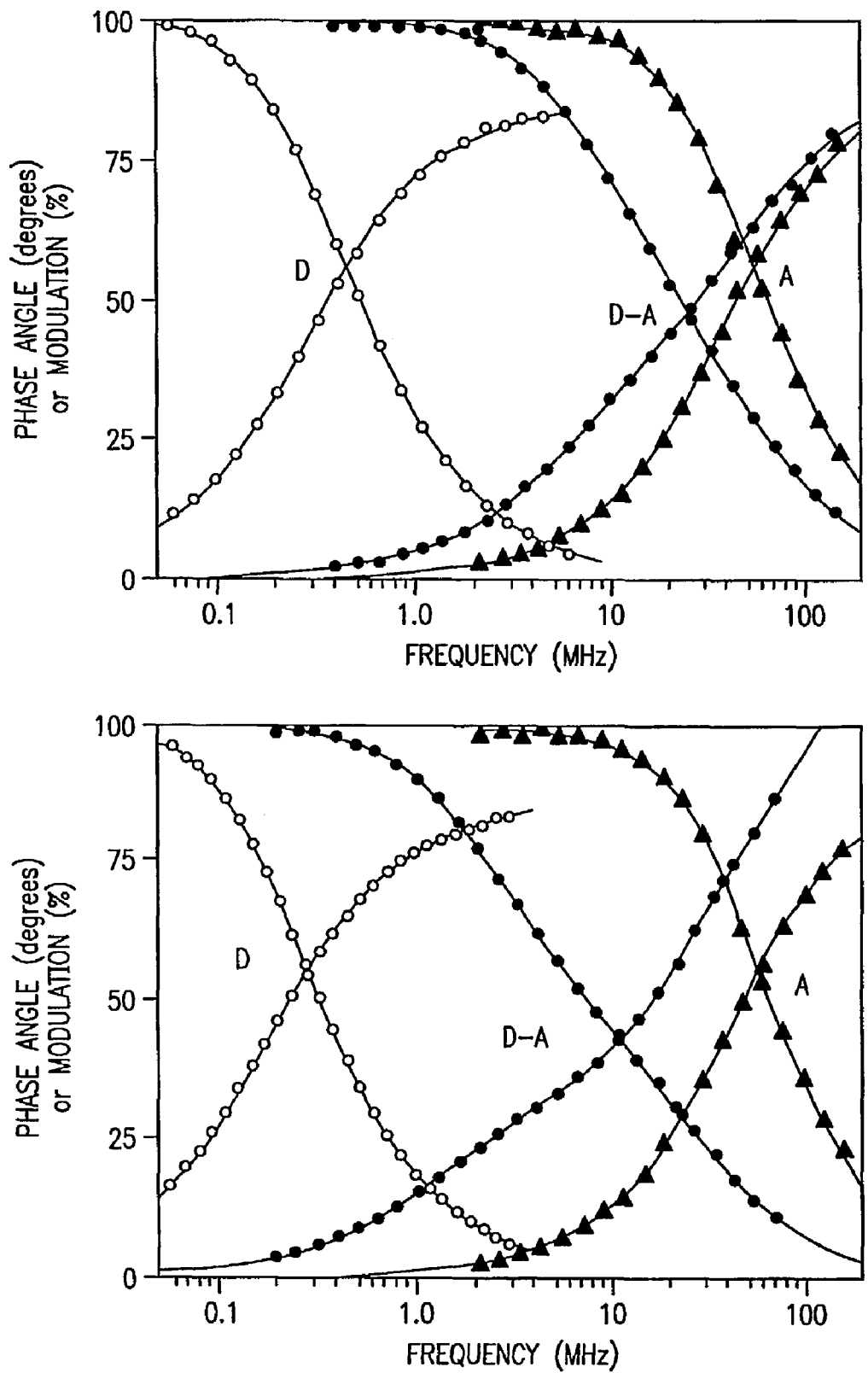
FIG. 8 shows the frequency domain intensity decays of the donor alone (D), acceptor alone (A) and of the covalently linked D-pro$_6$-A pair in aqueous buffer (top) and in propylene glycol (bottom).
Figure 9:
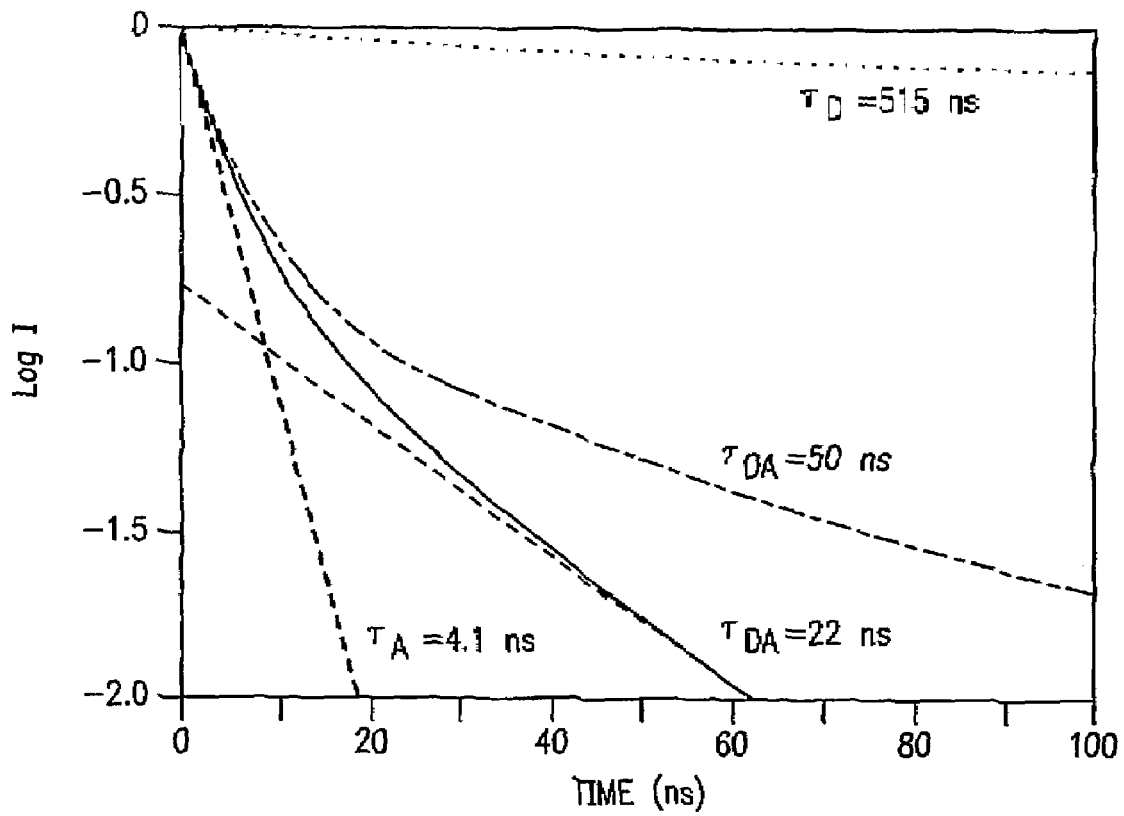
FIG. 9 shows the reconstructed time-domain intensity decays of the donor alone (D), acceptor alone (A) and the covalently linked pair (D-A) in water (top) and in propylene glycol (bottom); the solid line $t_{DA}$ is for D-pro$_6$-A and the dashed-dotted (-•-•-) line $t_{DA}$ is for D-pro$_8$-A.
Figure 9:
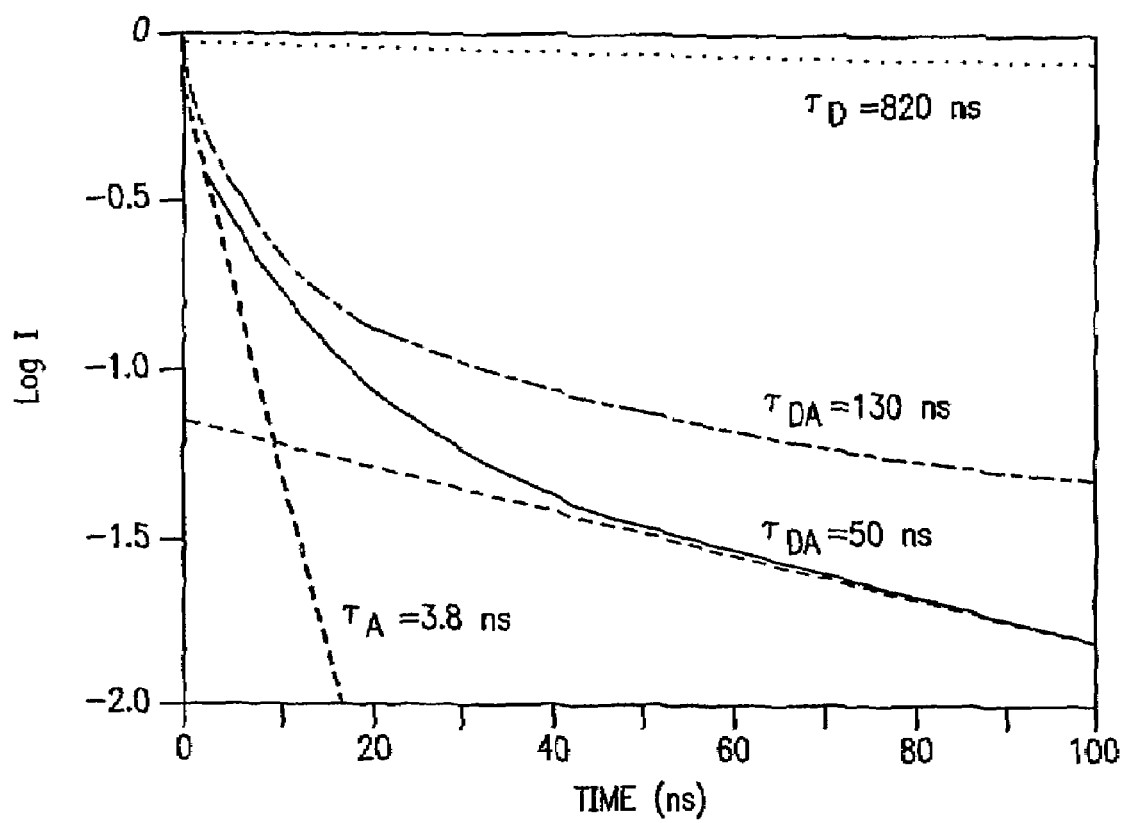

Data also showed that the enhanced red emission could be obtained with usefully long decay times. This is an important consideration because if the donor and acceptor are too close, or the rate of transfer is too fast, then the donor decay time will be shortened towards the ns value characteristic of the directly excited acceptor. The frequency-domain intensity decay of D, A and D-A are shown in water (FIG. 8, top) and in propylene glycol (bottom). For ease of understanding, the frequency-domain data were used to reconstruct the time-dependent decays (FIG. 9). In the absence of acceptor, the donor-alone displays a mostly single exponential decay with a decay time of 515 ns (top). The donor decay time is longer in propylene glycol (bottom), near 820 ns. The decay time of the directly excited acceptor is much shorter and near 4 ns in either solvent.

Figure 10:
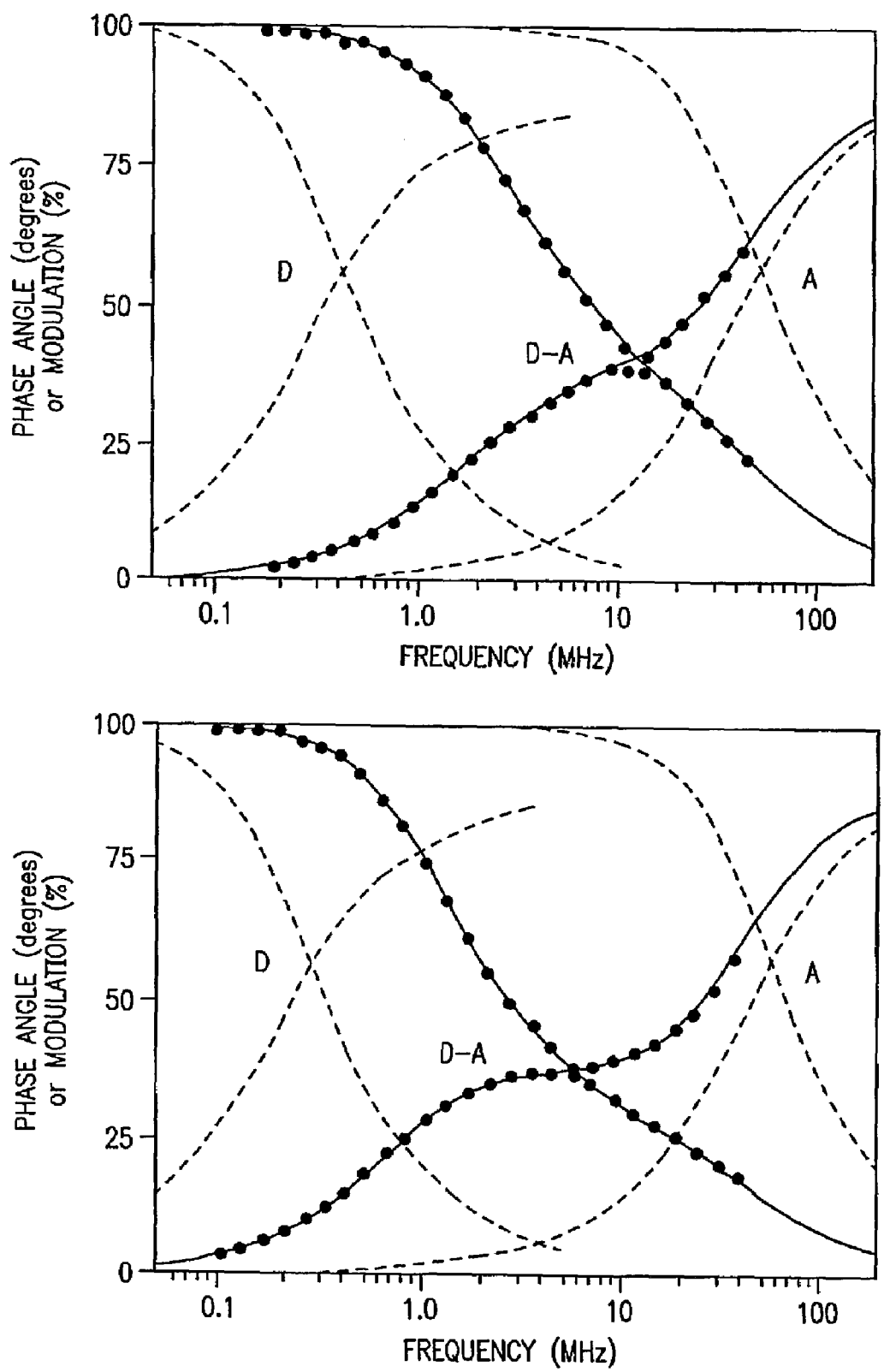
FIG. 10 shows the frequency domain intensity decays of the donor alone (D), acceptor alone (A) and of the covalently linked D-pro$_8$-cys-A pair in the aqueous buffer (top) and in propylene glycol (bottom).

The D-A pair measured at the acceptor emission wavelength displays a more complex intensity decay, as can be seen from the frequency responses for D-pro$_6$-A (FIG. 8) or D-pro$_8$-A (FIG. 9). The acceptor in D-pro$_8$-A displays a longer decay time as seen from the shift to lower frequency of D-pro$_8$-A as compared to D-pro$_6$-A The reconstructed intensity decays are shown in FIG. 10 and the intensity decay parameters are summarized in Table II. For a D-A pair at a single distance, a single decay time is expected for the donor. The heterogeneous decays of the D-A pairs is probably the result of a range of D-to-A distances due to the flexibility of the linkers between hexaproline and the probes. There are 12 chemical bonds between the last proline and Texas Red. When using an acceptor with a shorter linker, a more mono-exponential decay will result. Nonetheless, the D-pro$_6$-A displays a long decay time near 22 ns in water and 55 ns in propylene glycol. The components are assigned as due to the acceptors which are being excited by the excited donor population. A greater than 10-fold reduction in the donor decay time due to RET is consistent with the greater than 90% RET efficiency shown by this D-A pair.

Similar data were collected for the larger D-A pair with the $pro_8$ spacer, D-$pro_8$-A (Table II). The frequency-domain data are shown in FIG. 9 and the time-domain representations are shown in FIG. 10. For this more widely spaced D-A pair the acceptor shows a decay time of 50 ns in water and 130 ns in propylene glycol. Hence long decay times exceeding 100 ns can be obtained using such tandem luminophores.

TABLE I

Expected Lifetimes and Total Quantum Yields for D-A pairs[a]

| Transfer Efficiency | Acceptor Fluorescence Lifetimes | | Total Quantum Yield of the System |
|---|---|---|---|
| E | $\tau_1$ [ns] | $\tau_2$ [ns] | $Q_T = Q_D + Q_A$ |
| 0 | 10 | — | 0.108 |
| 0.091 | 10 | 909 | 0.180 |
| 0.333 | 10 | 667 | 0.372 |
| 0.500 | 10 | 500 | 0.504 |
| 0.667 | 10 | 333 | 0.636 |
| 0.833 | 10 | 167 | 0.768 |
| 0.909 | 10 | 91 | 0.829 |
| 0.950 | 10 | 48 | 0.860 |
| 0.980 | 10 | 20 | 0.884 | a $\tau_D^0 = 1000$ ns, $\tau_A^0 = 10$ ns, $Q_D^0 = 0.02$, $Q_A^0 = 0.90$. For these calculations we assumed the extinction coefficient of the donor is 9-fold larger than that of the acceptor, at the excitation wavelength.

TABLE II

Multi-exponential intensity decay analysis for the donor, acceptor and DA pairs shown in Scheme I[a]

| Solvent/ Compound Water | Q | $\alpha_i$[b] | $f_i$ | $\tau_i$ | $\chi_R^2$ |
|---|---|---|---|---|---|
| D-$pro_6$ | 0.0333 | 0.099 | 0.009 | 41.2 | 1.45[c] |
|  |  | 0.901 | 0.991 | 516.7 |  |
| $pro_6$-A | 0.360 | 1.0 | 1.0 | 4.0 | 1.26 |
| D-$pro_6$-A | 0.33 | 0.469 | 0.198 | 3.5 | 0.82 |
|  |  | 0.353 | 0.304 | 7.0 |  |
|  |  | 0.178 | 0.458 | 22.7 |  |
| D-$pro_8$-A | — | 0.784 | 0.287 | 4.4 |  |
|  |  | 0.137 | 0.252 | 22.3 |  |
|  |  | 0.079 | 0.461 | 71.1 |  |
| Propylene Glycol |  |  |  |  |  |
| D-$pro_{-6}$ | — | 0.125 | 0.014 | 79.4 | 0.98 |
|  |  | 0.875 | 0.986 | 785 |  |
| $pro_6$-A | — | 1.0 | 1.0 | 4.1 | 2.36 |
| D-$pro_6$-A | — | 0.803 | 0.363 | 7.9 |  |
|  |  | 0.178 | 0.245 | 33.4 |  |
|  |  | 0.069 | 0.392 | 99.5 | 0.51 |
| D-$pro_8$-A | — | 0.839 | 0.225 | 5.1 | 1.3 |
|  |  | 0.089 | 0.170 | 36.3 |  |
|  |  | 0.072 | 0.604 | 157.8 |  |

[a] Excitation was at 455 nm using a blue light emitting diode. The emission was measured at 630 nm with a 25 nm bandpass.
[b] The decays were analyzed internally at the multi-exponential model, $I(t) = \Sigma 3\alpha_i \exp(-t/\tau_i)$, $f_1 = \alpha_i\tau_i/\Sigma\alpha_j\tau_j$
[c] $\delta p = 0.3°$ and $\delta m = 0.003$.

EXAMPLE 3

Materials: CT-DNA, Tris.HCl and EDTA was obtained from Sigma (St. Louis, Mo.). Ru-BD was synthesized by the method described previously [51,52]. AO, EB, TOTO-3 and TO-PRO-3 were purchased from Molecular Probes (Eugene, Oreg.) and NB was from Aldrich (Milwaukee, Wis.). All reagents were used without further purification and water was deionized with a Milli-Q system. To convert CT-DNA into linear fragments comparable in length to one persistent length, about 5 mg/ml solution of CT-DNA was sonicated approximately 10 min while submerged in an ice bath. The sonicated DNA solution was centrifuged for 1 hr at 75,000 ×g to remove titanium particles and undissolved DNA. All experiments were undertaken at room temperature in 2 mM Tris.HCl, pH 8.0, containing 0.1 mM EDTA.

Absorption and steady-state fluorescence measurement: AO, EB and Ru-BD served as donors and NB, TOTO-3 and TO-PRO-3 were used as acceptors. About 5-10 mM stock solutions of AO, Ru-BD and NB were prepared in dimethylformamide and about a 10 mM stock solution of EB were made in DMSO. The final DMF concentration in all solutions was less than 1% (v/v). The concentration of DNA was quantified using a molar extinction coefficient of 13,300 $M^{-1}$ $cm^{-1}$ (expressed as bp) at 260 nm. The DNA concentration was 1 mM bp while the concentrations of AO, EB and Ru-BD were 5, 10 and 20 µM, respectively. Concentration of the probes were determined using the extinction coefficients in Table III. The highest acceptor concentrations of Ru-BD/NB, Ru-BD/TOTO-3, and Ru-BD/TO PRO-3 D-A pairs were 120, 60 and 120 µM, respectively. Because TOTO-3 and TO-PRO-3 were supplied as 1 mM stock solutions in DMSO, the maximum percentages of DMSO in the Ru-BD/TOTO-3 and Ru-BD/TO-PRO-3 D-A pairs were 6 and 12%(v/v), respectively. In preliminary experiments, we found that DMSO increased the steady-state fluorescence intensity of RuBD (data not shown). Hence, we added aliquots of DMSO to obtain 6 and 12%(v/v) DMSO in all Ru-BD/TOTO-3 and Ru-BD/TO-PRO-3 D-A pairs, respectively, to equalize the effect of DMSO. UV-visible absorption spectra were measured with a Hewlett-Packard 8453 diode array spectrophotometer with ±1 nm resolution. Steady-state fluorescence measurements were carried out using an Aminco SLM AB2 spectrofluorometer (Spectronic Instruments, Inc., IL) under magic angle conditions. The excitation wavelengths of AO, EB and RuBD were 470, 518 and 440 nm, respectively.

Figure 18:
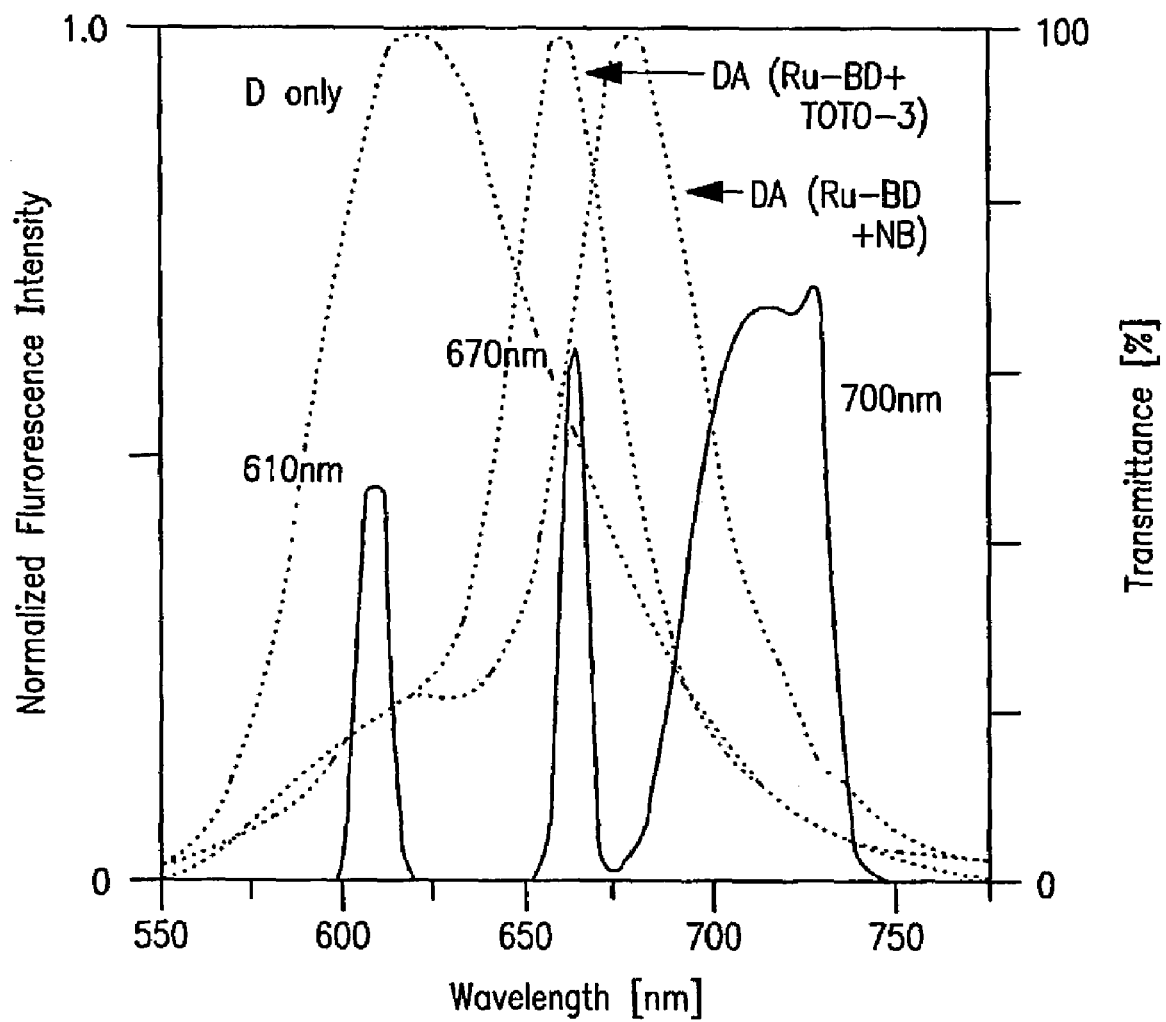
FIG. 18. Transmission spectra of the emission filters used for measuring the frequency-domain intensity decays (_____). The dashed lines show representative emission spectra of the donor alone (D) and donor plus acceptor (DA) samples.

Frequency-domain fluorescence measurements: Measurements were performed using the instruments described previously [75] and modified with a data acquisition card from ISS, Inc. (Urbana, Ill.) [76]. The excitation source was a blue LED LNG992CFBW (Panasonic, Japan) with luminous intensity of 1,500 mcd, and an LED driver LDX-3412 (ILX Lightwave, Boseman, Mo.) provided 30 mA of current at frequencies from 1 to 9.3 MHz. A 450RD55 interference filter (Omega Optical, Inc., Brattleboro, Vt.) and a 4-96 color glass filter (Corning Glass Work, Corning, N.Y.) were used to isolate the excitation wavelength. Rhodamine B in water was utilized as a lifetime standard. The transmission curves of the filters for isolating the emission from the donor, D-A pairs, and acceptors are shown below (FIG. 18).

Steady State Spectra

Figure 13:
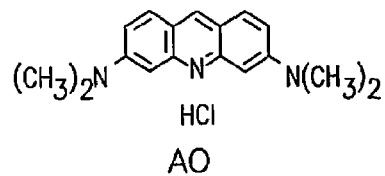
FIG. 13. Chemical structures of the donors and acceptors used in this report.
Figure 13:
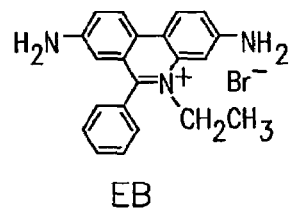
Figure 13:
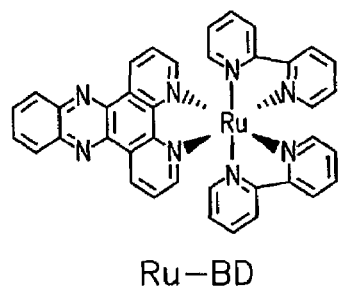
Figure 13:
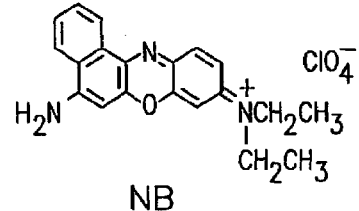
Figure 13:
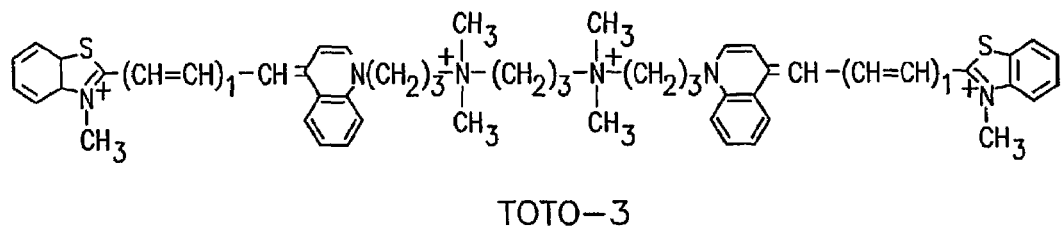
Figure 13:
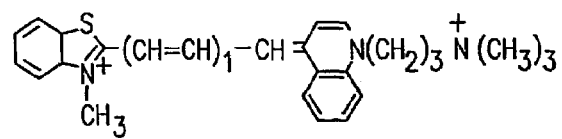

DNA with non-covalently bound donors and acceptors was used to test the possibility of creating long lifetime luminophores with high quantum yields. Three donors, acridine orange (AO), ethidium bromide (EB) and $[Ru(bpy)_2dppz]^{2+}$ (Ru-BD) were chosen. These structures are shown in FIG. 13. When bound in DNA the quantum yields decrease in this respective order (Table III). Acceptors, were nile blue (NB), TOTO-3 and TO-PRO-3 (FIG. 13), which display increasing quantum yields in the listed order. Dyes non-covalently bound to DNA were used because this approach allowed us to select donors and acceptors with various quantum yields, without the need for chemical synthesis. Also, this approach allowed us to adjust the concentrations of donors and acceptors to observe trends in the spectra. Based on the theory described above, the largest overall increase in the total emission of the tandem luminophore was expected to occur with RET between the lowest quantum yield donor (Ru-BD) and the highest quantum yield acceptor (TO-PRO-3).

Figure 14:
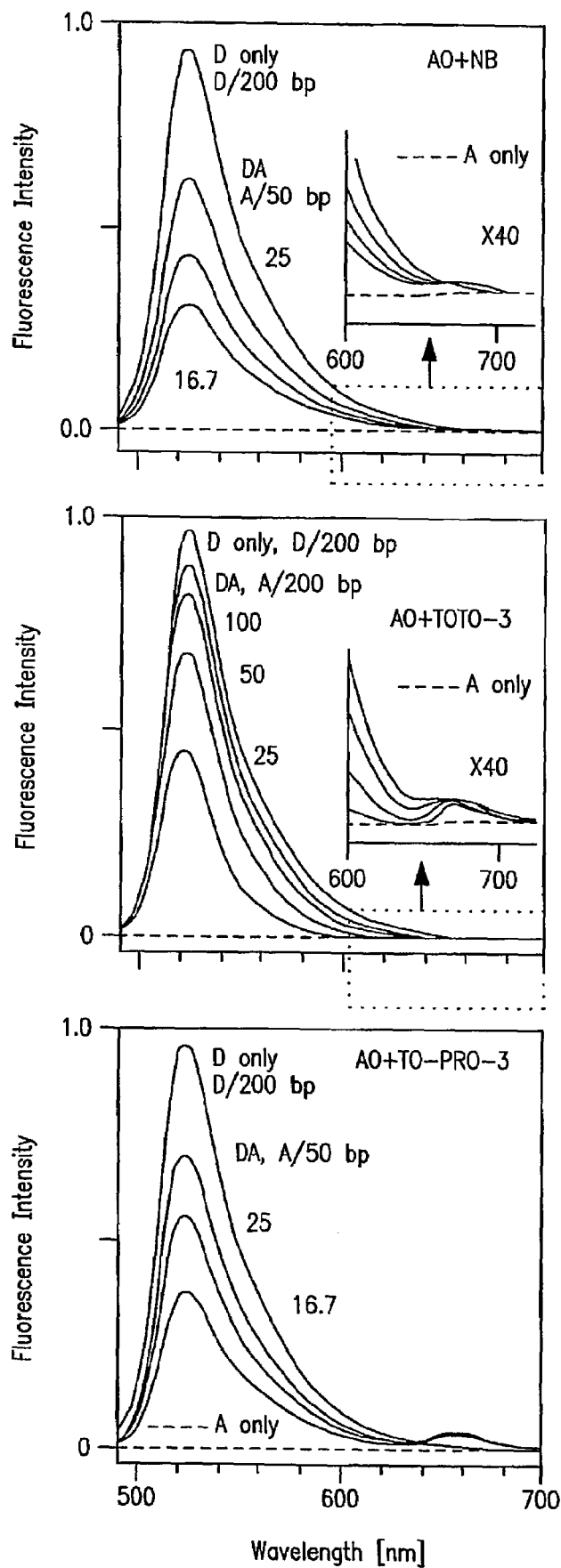
FIG. 14. Emission spectra of the acridine orange donor [Donor]=5 µM bound to DNA in the presence of the acceptors nile blue (top), TOTO-3 (middle), or TO-PRO-3 (bottom). The inserts show the acceptor region with the amplitude increased by a factor of 40. The dashed lines show the emission of acceptor-alone with DNA, but without donor, at the highest acceptor concentration used in the figure. The donor is present at 1 donor per 200 base pairs. The number for the donor-acceptor (DA) pair is the number of base pairs for each acceptor.

FIG. 14 shows the emission spectra of AO bound to DNA with increasing amounts of acceptor. With the high quantum yield AO donor the NB acceptor emission is almost undetectable (FIG. 14, top insert). The quantum yield of the TOTO-3 acceptor is higher than that of NB, and the quantum yield of TO-PRO-3 is higher still. The acceptor emission becomes more easily detectable as the acceptor quantum yields increase. In each case the observed acceptor emission is due to RET from the donor. No significant acceptor emission was found for the acceptors bound to DNA in the absence of donor (dashed lines). An interesting aspect of FIG. 14 is that RET from a high quantum yield donor (AD) to a low quantum yield acceptor (NB) decreases the total emission from the donor and acceptor.

Figure 15:
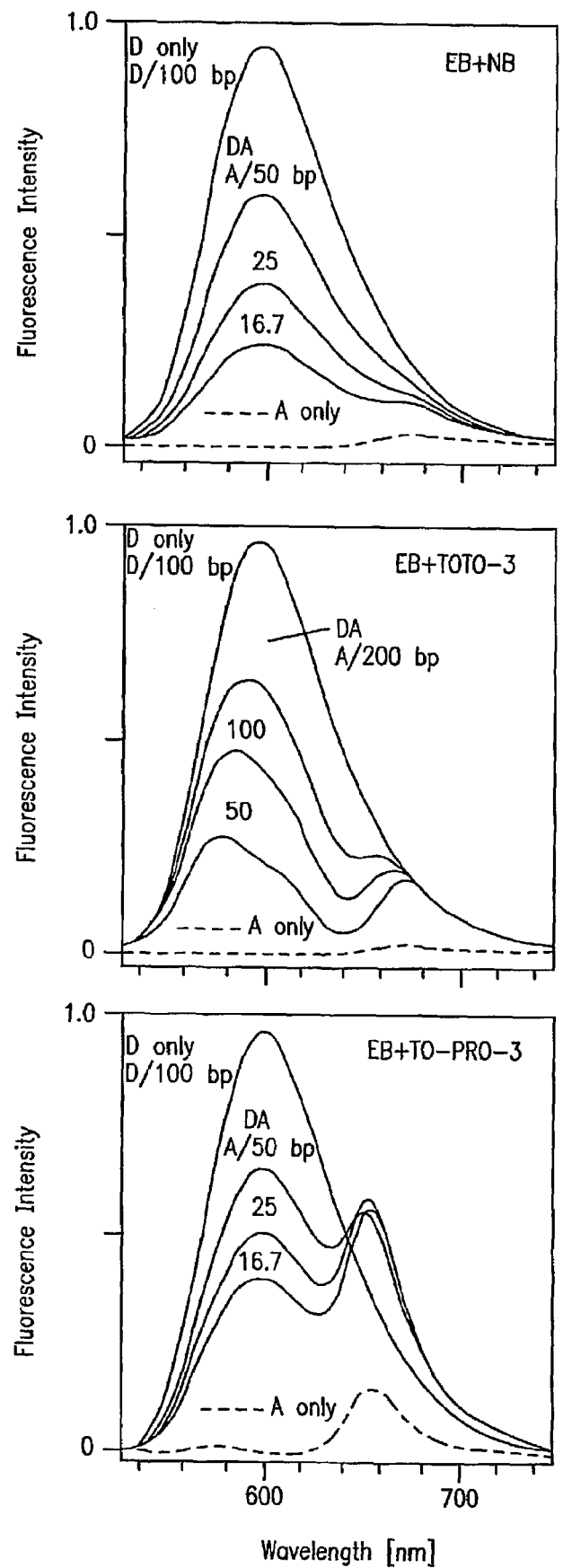
FIG. 15. Emission spectra of ethidium bromide donor [Donor]=10 µM bound to DNA in the presence of the acceptors nile blue (top), TOTO-3 (middle) or TO-PRO-3 (bottom). The dashed lines show the emission of the acceptor-alone with DNA, but without donor, at the highest used acceptor concentration. The donor is present at 1 donor per 100 base pairs. The number for the donor-acceptor (DA) pair is the number of base pairs for each acceptor.
Figure 16:
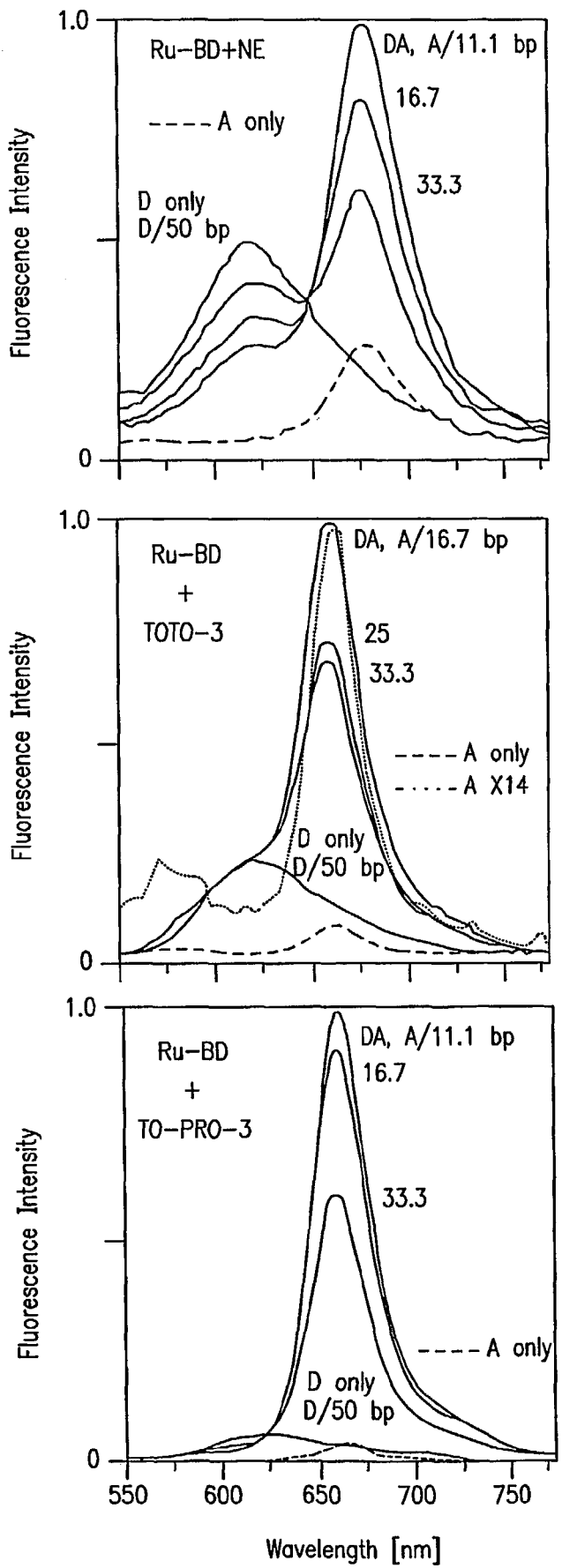
FIG. 16. Emission spectra of Ru-BD([Ru(bpy)$_2$dppz]$^{2+}$) donor [Donor]=20 µM bound to DNA in the presence of the acceptors nile blue (top), TOTO-3 (middle) and TO-PRO-3 (bottom). The dashed lines show the emission spectra of the acceptor-alone with DNA, but without donor, at the highest used acceptor concentration. One donor is present per 50 base pairs. The number for the donor-acceptor (DA) pair is the number of base pairs for each acceptor.

FIGS. 15 and 16 show emission spectra with the same acceptors, but with EB and Ru-BD as the donors. Examination of these spectra shows that the enhancement of the acceptor emission is larger for Ru-BD than for EB. Also, the largest enhancements are seen for TO-PRO-3, the acceptor with the highest quantum yield (FIG. 16, lower panel). In this case the acceptor emission is increased many-fold by energy transfer from the Ru-BD donor. Also, the emission from the D-A system is considerably larger than that of the donor alone bound to DNA, or the acceptor alone bound to DNA (dashed line). This effect is the opposite of that found for the AO/NB D-A pair. In this case the weakly fluorescent NB received most of the energy by RET, but still emits with its own low quantum yield. For the Ru-BD/TO-PRO-3 D-A pair the strongly fluorescent TO-PRO-3 receives most of the energy absorbed by the donor, in spite of the low intrinsic quantum yield of the donor.

Figure 17:
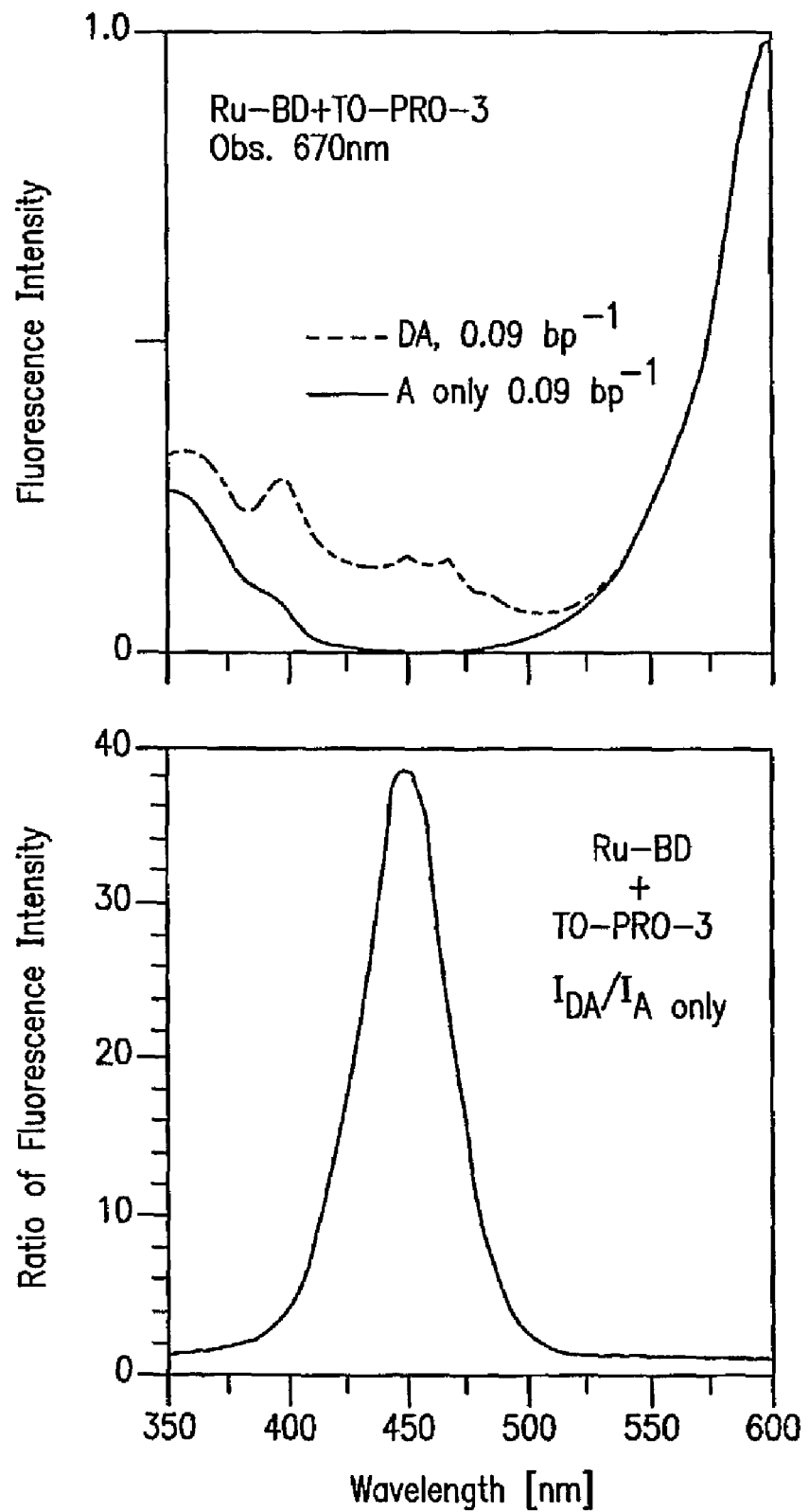
FIG. 17. Uncorrected excitation spectra of Ru-BD and TO-PRO-3 bound to DNA (- - -), and of TO-PRO-3 alone bound to DNA (_____). The lower panel shows the ratio of the two excitation spectra.

In the absence of energy transfer the intensity of the acceptor is proportional to $\epsilon_A Q_A$, where $\epsilon_A$ refers to the extinction coefficient of the acceptor at the donor excitation wavelength. If transfer is 100% effective the intensity of the acceptor is proportional to $(\epsilon_A+\epsilon_D)/\epsilon_A$. According to Table III this ratio is near 4. Examination of FIG. 16 (lowest panel) indicates that the acceptor enhancement is greater than 4, surprisingly. To further this effect the excitation spectra of the D-A pair, and the acceptor alone, when bound to DNA were examined. On the same relative scale the acceptor alone displays essentially no emission upon excitation at 450 nm (FIG. 17). The lower panel shows the ratio of these excitation spectra, which becomes close to 40 at 450 nm. This ratio is larger than expected from the extinction coefficients listed in Table III. It appears that excitation of TO-PRO-3 near 450 nm results in less emission than predicted by its absorption spectrum. This effect could be due to the presence of non-flourescent absorbing impurities, or absorption of non-fluorescent conformers of TO-PRO-3 at 450 nm. It is known that this class of dyes display weak fluorescence in water or when there is torsional motions about the central methine bridge [77]. Irrespective of the origin of this low intensity, the acceptor enhancement seen in FIG. 16 is consistent with the excitation spectrum for this D-A pair.

Time-Resolved Decays

Frequency-domain intensity decays were measured through filters selected to isolate the desired emission wavelengths (FIG. 18). Observation at 610 nm results in selective observation of the donor emission, and observation at 670 or 700 nm selects the acceptor emission.

Figure 19:
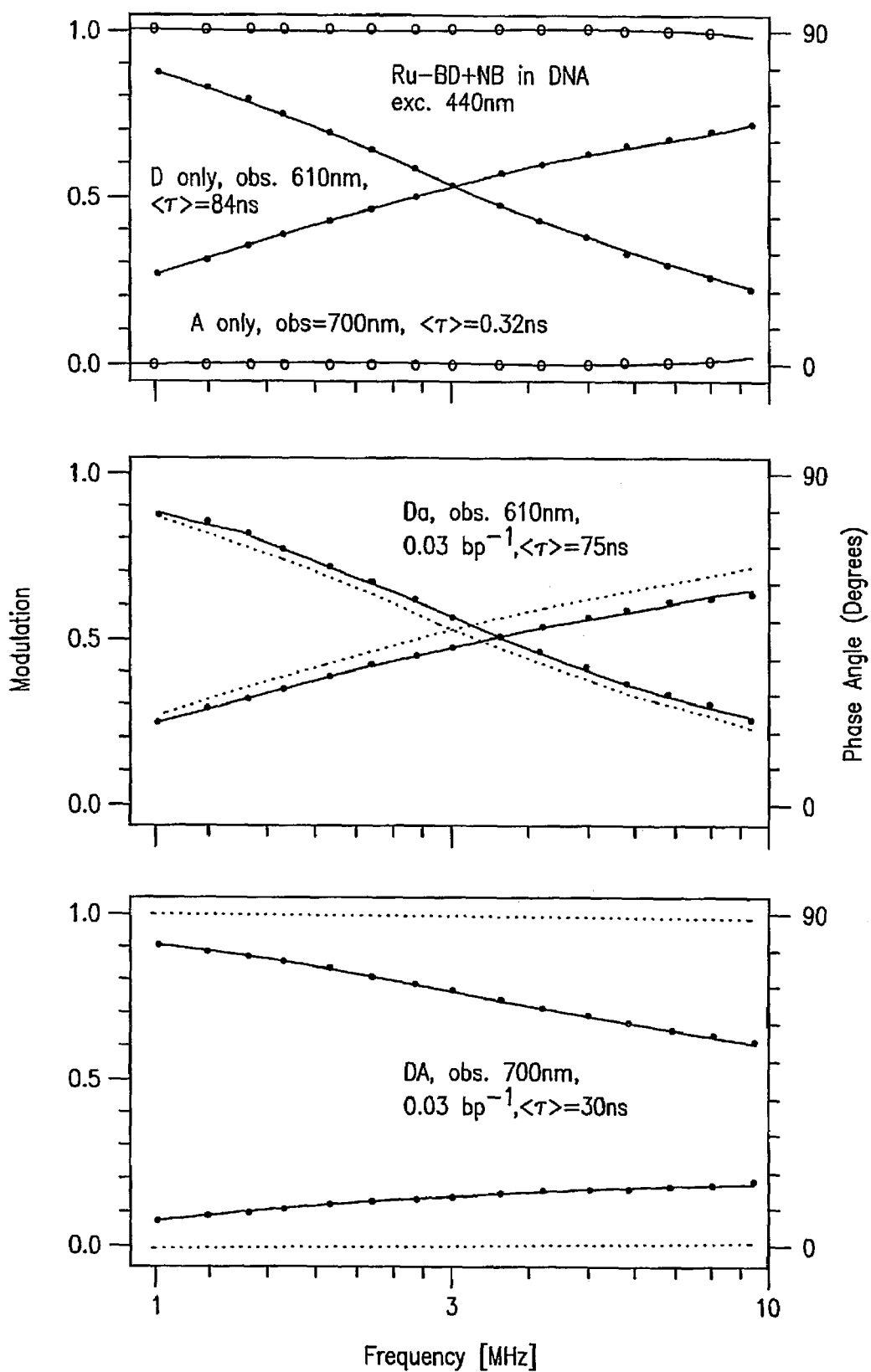
FIG. 19. Frequency-domain intensity decays of Ru-BD bound to DNA in the absence and presence of the nile blue acceptor. The solid dots represent the phase or modulation values and the solid lines the best multi-exponential fits to the data. In the middle and lower panels the dotted lines represent the donor-alone and acceptor-alone frequency responses, respectively.
Figure 20:
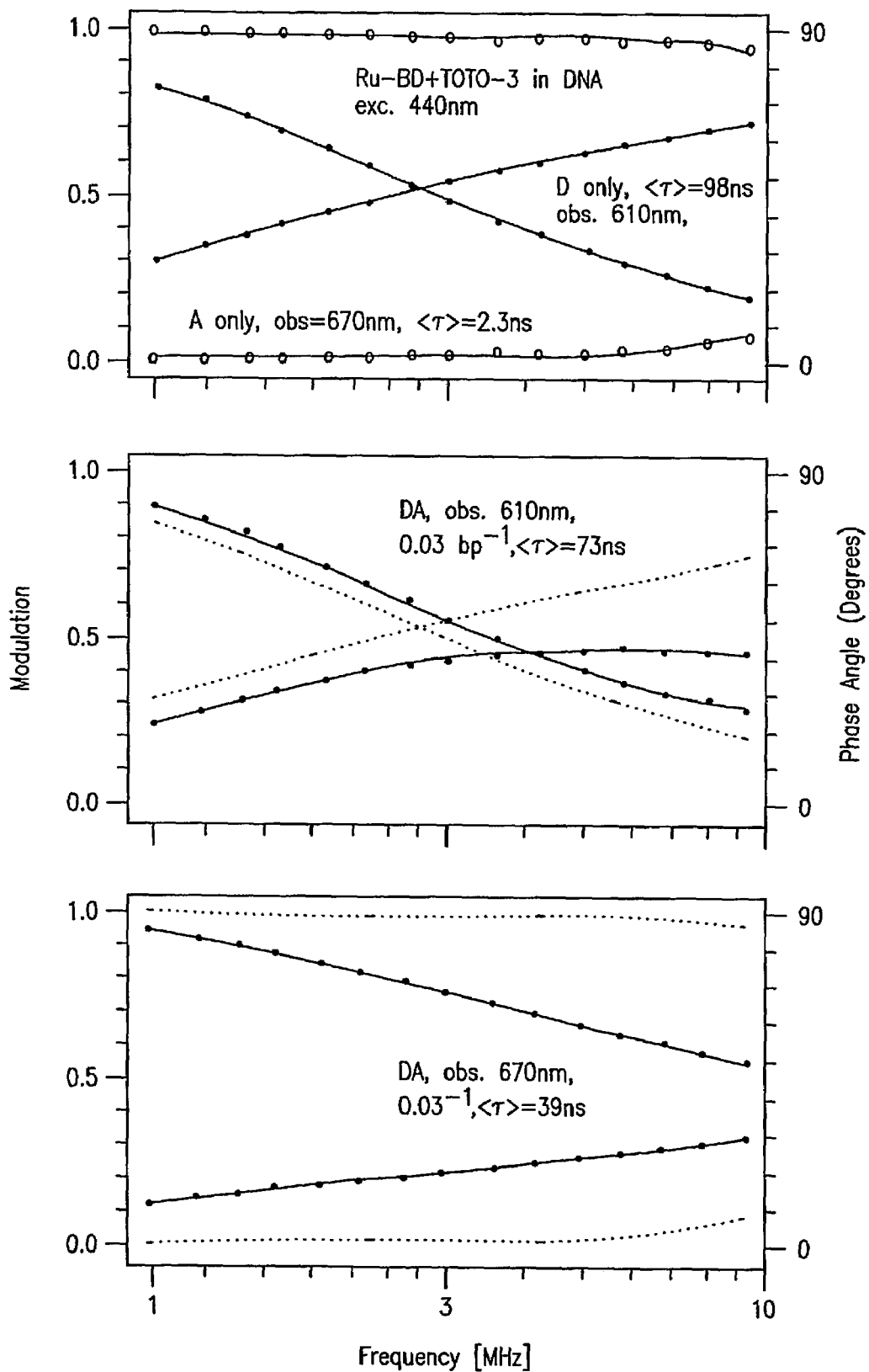
FIG. 20. Frequency-domain intensity decay of Ru-BD bound to DNA in the absence and presence of the TOTO-3 acceptor. See legend to FIG. 7.
Figure 21:
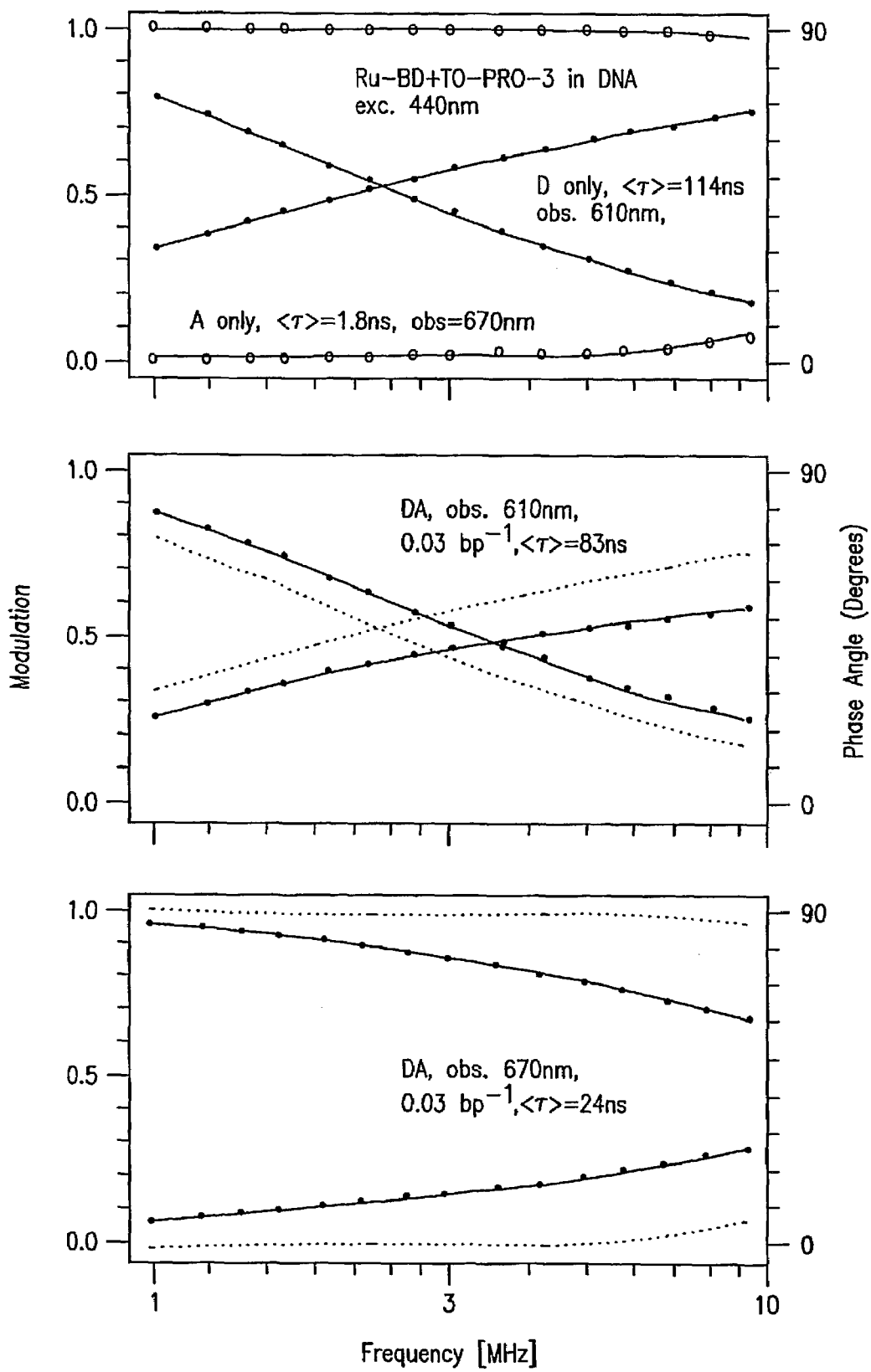
FIG. 21. Frequency-domain intensity decay of Ru-BD bound to DNA in the absence and presence of the TO-PRO-3 acceptor. See legend to FIG. 7.

FIGS. 19-21 show the frequency-domain data for three D-A pairs. In these data Ru-BP is always the donor. The acceptor is NB, TOTO-3 or TO-PRO-3, respectively. In the absence of acceptors, the mean Ru-BD lifetime is near 100 ns (Table IV). The Ru-BD lifetime is only moderately decreased by the acceptor. For instance, for any of the acceptors, a ratio of 0.03 acceptors per base pair results in a mean donor lifetime is near 70 ns. This was initially surprising given the 2-fold or larger quenching of the Ru-BD intensity by these acceptor concentrations. However, this difference in intensity and lifetime quenching can be explained as due to a range of D-to-A distances in the labeled DNA. More specifically, most of the acceptor emission results from the more closely spaced D-A pairs. In contrast, the observed donor emission in the presence of acceptors is increased by the higher intensities of those donors most distant from acceptors, which are also the donors with the longer lifetimes.

The lower panels of FIGS. 19-21 shows the frequency response observed for the longer wavelength regions dominated by the acceptor emission. In each case the mean decay times are near 30 ns for observation at the acceptor emission wavelengths. While the frequency responses are multi-exponential, visually obvious contributions from the directly excited acceptors with their 0.3 to 2.3 ns lifetimes were not found. The apparent acceptor lifetimes are shorter than the apparent donor lifetimes because the acceptor emission is enriched for the shorter distances D-A pairs which have a shorter donor lifetime.

Figure 22:
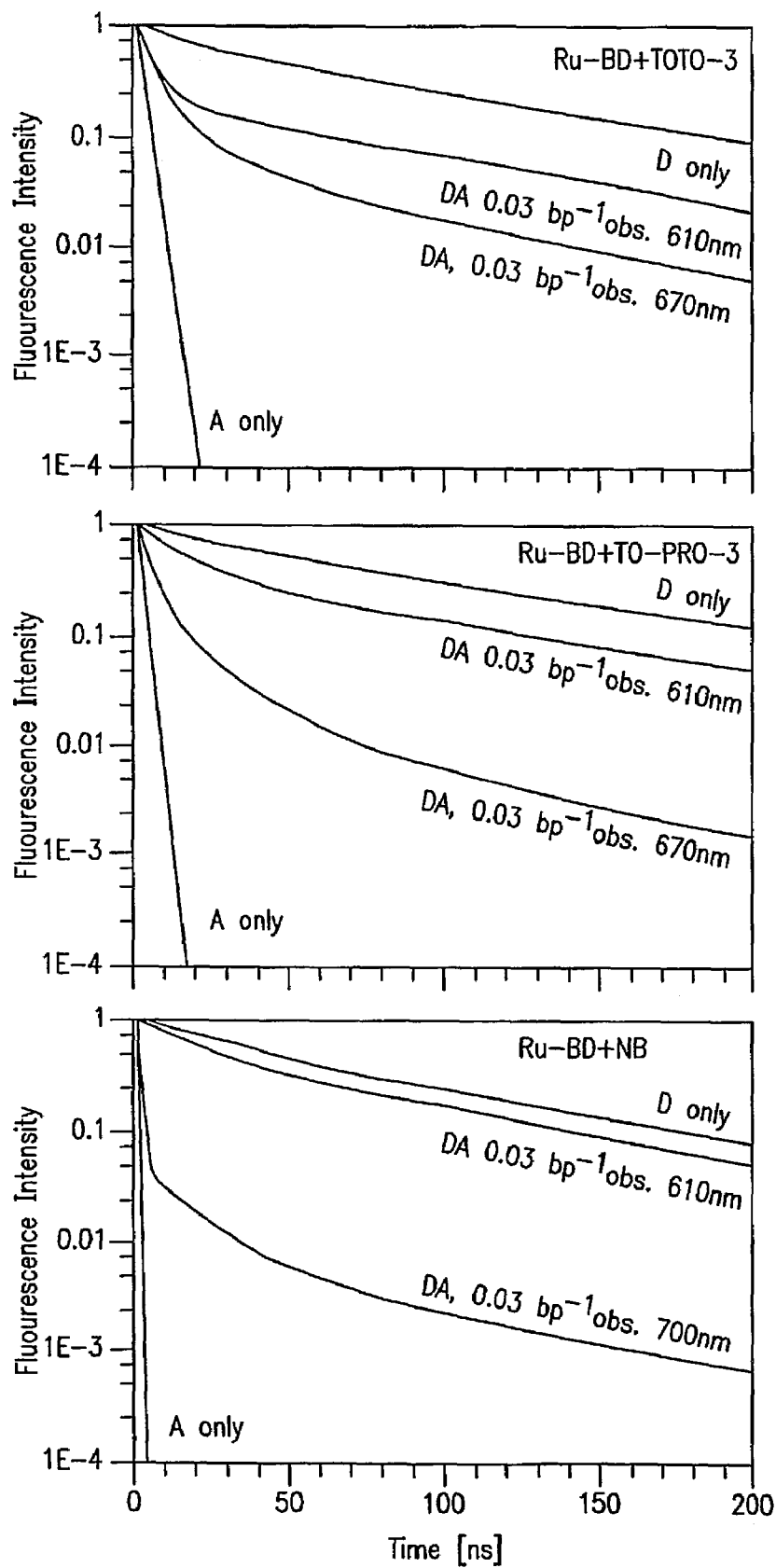
FIG. 22. Time-domain intensity decay of Ru-BD and acceptor complexes with DNA.

It is informative to examine the intensity decays in the time-domain reconstructed from the frequency-domain data (FIG. 22). The decays of the directly excited acceptors are short, and emission from the directly excited acceptors will not be observed if the detection is off-gated for the first 10-20 ns following the excitation pulse. The donor decays, even in the presence of acceptors, are long lived. Also, following a brief transition period out to 10-40 ns, the acceptor decay rates are comparable to that of the quenched donors. This long lived emission from the donors can be used for biophysical or analytical purposes.

An important conclusion from these experiments is that the apparent acceptor decays are adequately long for off-gating of the autofluorescence from biological samples. Hence the use of MLC-acceptor pairs provides an opportunity to obtain luminophores which display long lifetimes, high quantum yields, and long emission wavelengths.

By consideration of the well known characteristics of Förster transfer, one can predict that suitable designed D-A pairs will display even more favorable properties. For instance, the acceptor decay times for the DNA bound probes were shorter than the donor decay times. This effect is due to a range of donor-to-acceptor distances for the probes randomly bound to DNA. It is well known that unique D-to-A distances can be obtained with polyproline spacers [53] or with double-stranded DNA as the spacer [54-55]. In such cases the donor decay times will decrease in proportion to the transfer efficiency, and the acceptor decay times will be similar to the donor decay times. The results for a donor and acceptor separated by a single distance are expected to be comparable to that shown in FIG. 11, where a 1 μs decay time donor, with 90% transfer efficiency, results in a luminophore with a 100 ns lifetime. Since metal-ligand complexes are known with decay times as long as 42 μs [56-57], one can predict 4 μs decay time luminophores with 90% transfer.

Another advantage of these RET probes is that the emission spectra of red and NIR fluorophores are typically narrow on the wavelength scale, whereas the emission spectra of the MLCs are broad. Since autofluorescence from biological samples is typically broader distributed broadly on the wavelength scale, the concentration of the emission into a narrow spectral range by the acceptor will improve detectability of these luminophores.

TABLE III

Quantum Yields (Q), Decay Times (τ) and Molar Extinction Coefficients ($\epsilon/\lambda_{max}$) of Fluorophores in DNA

| Probe | Donor/Acceptor | $Q^a$ | $\tau$ (ns) | $\epsilon/\lambda_{ex}$ ($M^{-1}cm^{-1}$/nm) | $\epsilon/\lambda_{max}$ ($M^{-1}cm^{-1}$/nm) |
|---|---|---|---|---|---|
| AO | Donor | 0.392 | 5.0 | 23,300/470 | 53,000/500 |
| EB | Donor | 0.219 | 21.9 | 5,200/518 | 5,200/518 |
| RuBD | Donor | 0.008 | 84.0 | 13,000/440 | 13,000/440 |
| NB | Acceptor | 0.004 | 0.32 | 1,180/440 | 42,900/656 |
| TOTO-3 | Acceptor | 0.06 | 2.3 | 2,240/440 | 154,000/642 |
| TO-PRO-3 | Acceptor | 0.11 | 1.8 | 200/440 | 102,000/642 |

$^a$The following compounds were used as quantum yield references: in the case of AO, 3-aminofluoranthene in DMSO (Q = 0.32); EB in methanol (Q = 0.06) for EB; 4-dicyanomethylene-2-methyl-6-(p-dimethylaminostyryl)4H-pyran in methanol (Q = 0.38) in the case of RuBD and NB; and fluorescein in 0.1 M NaOH (Q = 0.92) for TOTO-3 and TO-PRO-3.
$^b$Mean lifetime calculated using $\bar{\tau} = \Sigma f_i \tau_i$, where $f_i$ is the fractional steady state contribution of each component to the total emission.
$^c$From Molecular Probes, Inc.

TABLE IV

Multi-exponential intensity decay analyses of the Ru-BD donor and acceptors bound to calf thymus DNA.

| Donor/Acceptor | $n^a$ | $<\tau>^b$ | $\alpha_i$ | $f_i$ | $\tau_i$ | $\chi_R^2$ |
|---|---|---|---|---|---|---|
| Ru-BD/NB$^c$ | | | | | | |
| Ru-BD | 2 | 84 | 0.36 | 0.13 | 24 | 0.91 |
|  |  |  | 0.64 | 0.87 | 93 |  |
| NB | 1 | 0.32 | 1.00 | 1.00 | 0.32 | 0.85 |
| DA Obs. 610 nm | 2 | 75 | 0.50 | 0.15 | 16 | 1.40 |
|  |  |  | 0.50 | 0.85 | 86 |  |
| DA Obs. 700 nm. | 3 | 30 | 0.95 | 0.51 | 1.9 | 0.90 |
|  |  |  | 0.04 | 0.21 | 22 |  |
|  |  |  | 0.01 | 0.28 | 87 |  |
| Ru-BD/TOTO-3$^c$ | | | | | | |
| Ru-BD | 2 | 98 | 0.42 | 0.18 | 33 | 0.99 |
|  |  |  | 0.58 | 0.82 | 111 |  |
| TOTO-3 | 1 | 2.3 | 1.00 | 1.00 | 2.3 | 1.30 |
| DA Obs. 610 nm | 2 | 73 | 0.79 | 0.19 | 5.8 | 1.07 |
|  |  |  | 0.21 | 0.81 | 90 |  |
| DA Obs. 670 nm. | 3 | 39 | 0.83 | 0.41 | 5.6 | 1.02 |
|  |  |  | 0.12 | 0.24 | 23 |  |
|  |  |  | 0.05 | 0.35 | 88 |  |
| Ru-BD/TO-PRO-3$^c$ | | | | | | |
| Ru-BD | 2 | 114 | 0.42 | 0.17 | 38 | 1.02 |
|  |  |  | 0.58 | 0.83 | 130 |  |
| TO-PRO-3 | 1 | 1.8 | 1.00 | 1.00 | 1.8 | 1.02 |
| DA Obs. 610 nm | 2 | 83 | 0.62 | 0.19 | 14 | 0.81 |
|  |  |  | 0.38 | 0.81 | 99 |  |
| DA Obs. 670 nm. | 3 | 24 | 0.83 | 0.48 | 5.1 | 1.05 |
|  |  |  | 0.15 | 0.33 | 19 |  |
|  |  |  | 0.02 | 0.19 | 78 |  |

$^a$Number of decay times in the multi-exponential fit.
$^b<\tau> = \Sigma \tau_i f_i$ where $f_i$ is the steady state contribution of each component.
$^c$All acceptor concentrations are 0.03 bp$^{-1}$ The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

From the foregoing description, one skilled in the art can easily ascertain the essential characteristics of this invention, and without departing from the spirit and scope thereof, can make various changes and modifications of the invention to adapt it to various usages and conditions.

REFERENCES

1. Thompson, R. B. (1994). Red and near-infrared fluorometry, in *Topics in Fluorescence Spectroscopy, Vol. 4: Probe Design and Chemical Sensing* (J. R. Lakowicz, Ed.), Plenum Press, New York, pp. 151-222.
2. Daehne, S., Resch-Genger, U., and Wolfbeis, O. S. (1998). *Near-infrared Dyes for High Technology Applications*, Kluwer Academic Publishers, Boston, pp. 458.
3. Southwick, P. L., Ernst, L. A., Tauriello, E. W., Parker, S. R., Mujumdar, R. B., Mujumdar, S. W., Clever, H. A., and Waggoner, A. S. (1990), Cyanine dye labeling reagents-carboxymethylindocyanine succinimidyl esters, *Cytometry* 11:418-430.
4. Rahavendran, S. V., and Karnes, H. T. (1996). An oxazine reagent for derivatization of carboxylic acid analytes suitable for liquid chromatographic detection using visible diode laser induced fluorescence, *J. Pharm. Biomed. Anal.* 15:83-98.
5. Rahavendran, S. V., and Karnes, H. T. (1996). Application of rhodamine 800 for reversed phase liquid chromatographic detection using, visible diode laser induced fluorescence, *Anal. Chem.* 68:3763-3768.
6. Kessler, M. A., and Wolfbeis, O. S. (1992). Laser-induced fluorometric determination of albumin using longwave absorbing molecular probes, *Anal. Biochem.* 200:254-259.
7. Middendorf, L., Amen, J., Bruce, R., Draney, D., DeGraff, D., Gewecke, J., Grone, D., Humphrey, P., Little, G., Lugade, A., Narayanan, N., Oommen, A., Osterman, H., Peterson, R., Rada, J., Raghavachari, R., and Roemer, S. (1998). Near-infrared fluorescence instrumentation for DNA analysis, in *Near-Infrared Dyes for High Technology Applications*, (S. Daehen, Ed.), Kluwer Academic Publishers, Netherlands, pp. 21-54.
8. Flanagan, J. H., Romero, S. E., Legendre, B. L., Hammer, R. P., and Soper, A. (1997). Heavy-atom modified near IR fluorescent dyes for DNA sequencing applications: Synthesis and photophysical characterization, *SPIE* 2980:328-337.
9. Owens, C. V., Davidson, Y. Y., Kar, S., and Soper, S. A. (1997). High-resolution separation of DNA restriction fragments using capillary electrophoresis with near-IR; diode-based, laser-induced fluorescence detection, *Anal. Chem.* 69:1256-1261.
10. Abugo, O. O., Nair, R., and Lakowicz, J. R. (2000). Fluorescence properties of rhodamine 800 in whole blood and plasma, *Anal. Biochem.* 279:142-150.
11. Dorshow, R. B., Bugaj, J. E., Burleigh, B. D., Duncan, J. R., Johnson, M. A., and Jones, W. B. (1998). Noninvasive fluorescence detection of hepatic and renal function, *J. Biomed. Optics* 3(3):340-345.
12. Kanda, M., and Niwa, S. (1992). Development of a non-invasive monitoring instrument for serum Indocyanine Green dye concentration, *Appl. Optics.* 31(31):6668-6675.
13. Bollinger, A., Saesseli, B., Hoffmann, U., and Franzeck, U. K. (1991). Intravital detection of skin capillary aneurysms by videomicroscopy with Indocyanine Green in patients with progressive systemic sclerosis and related disorders, *Circulation* 83:546-551.
14. Strickler, S. J., and Berg, R. A. (1962). Relationship between absorption intensity and fluorescence lifetime of molecules, *J. Chem. Phys.* 37:814-822.
15. Kalayanasundarm, K. (1992). *Photochemistry of Polypyridine and Porphyrin Complexes*, Academic Press, New York,
16. Juris, A., Balzani, V., Barigelletti, F., Campagna, S., Belser, P., and Von Zelewsky, A. (1988). Ru(II) polypyridine complexes: Photophysics, photochemistry, electrochemistry, and chemiluminescence, *Coord. Chem. Rev.* 84:85-277.
17. Tyson, D. S., and Castellano, F. N. (1999). Intramolecular singlet and triplet energy transfer in a ruthenium(II) diimine complex containing multiple pyrenyl chromophores, *J. Phys. Chem. A.* 103:10955-10960.
18. Stiffens, D. J., Aarnts, M. P., Rossenaar, B. D., and Vlcek, A. (1997). A new series of Re- and Ru-complexes having a lowest $\sigma\pi^*$ excited state that varies from reactive to stable and long lived, *Pure & Appl. Chem.* 69(4):831-835.
19. Simon, J. A., Curry, S. L., Schmehl, R. H., Schatz, T. R., Piotrowiak, P. I, Jin, X., and Thummel, R. P. (1997). Intramolecular electronic energy transfer in ruthenium(II) diimine donor/pyrene acceptor complexes linked by a single C-C bond, *J. Am. Chem. Soc.* 119:11012-11022.
20. Harriman, A., Hissler, M., Khatyr, A., and Ziessel, R. (1999). A ruthenium(II) tris(2,2'-bipyridine) derivative possessing a triplet lifetime of 42 µs, *Chem. Commun.* 735-736.
21. Demas, J. N., and DeGraff, B. A. (1991). Design and applications of highly luminescent transition metal complexes, *Anal. Chem.* 63:829A-837A.
22. Demas, J. N., and DeGraff, B. A. (1994). Design and applications of highly luminescent transition metal complexes. In *Topics in Fluorescence Spectroscopy, Vol. 4: Probe Design and Chemical Sensing*, (J. R. Lakowicz, Ed.), Plenum Press, New York, pp. 71-107.
23. Terpetschnig, E., Szmacinski, H., Malak, H., and Lakowicz, J. R. (1995). Metal-ligand complexes as a new class of long lived fluorophores for protein hydrodynamics, *Biophys. J.* 68:342-350.
24. Szmacinski, H., Terpetschnig, E., and Lakowicz, J. R. (1996). Synthesis and evaluation of Ru-complexes as anisotropy probes for protein hydrodynamics and immunoassays of high-molecular weight antigens, *Biophys. Chem.* 62:109-120.
25. Guo, X-Q., Castellano, F. N., Li, L., and Lakowicz, J. R. (1998). Use of a long lifetime Re(I) complex in fluorescence polarization immunoassays of high-molecular weight analytes, *Anal. Chem.* 70:632-637.
26. Murtaza, Z., and Lakowicz, J. R. (1999). Long-lifetime and long-wavelength osmium(II) metal compounds containing polypyridine ligands. Excellent red fluorescent dyes for biophysics and sensors, *SPIE* 3602:309-315.
27. Grigg, R., and Norbert, W. D. J. A. (1992). Luminescent pH sensors based on di(2,2'-bipyridyl)(5,5'-diaminomethyl-2,2'-bipyridyl)-ruthenium(II) complexes, *J. Chem. Soc. Chem. Commun.* 1992:1300-1302.
28. Lippitsch, M. E., and Wolfbeis, O. S. (1988). Fiber-optics oxygen sensor with the fluorescence decay time as the information carrier, *Anal. Chim.* 205:1-6.
29. Ju, J., Ruan, C., Fuller, C. W., Glazer, A. N., and Mathies, R. A. (1995). Fluorescence energy transfer dye-labeled primers for DNA sequencing and analysis, *Proc. Natl. Acad. Sci. USA* 92:4347-4351.
30. Ju, J., Glazer, A. N., and Mathies, R. A. (1996). Energy transfer primers: A new fluorescence labeling paradigm for DNA sequencing and analysis, *Nat. Med.* 2(2):246-249.
31. Stryer, L. (1978). Fluorescence energy transfer as a spectroscopic ruler, *Annu. Rev. Biochem.* 47:819-846.
32. Clegg, R. M. (1996). Fluorescence resonance energy transfer, in *Fluorescence Imaging Spectroscopy and Microscopy*, (Wang, X. F., and Herman, B., Eds.), John Wiley & Sons, New York, pp.179-252.
33. Lakowicz, J. R. *Topics in Fluorescence Spectroscopy, 2$^{nd}$ edition*. Kluwer Academic/Plenum Publishers, New York, pp. 698. Chapters 13-15, pp. 367-443.
34. Laws, J. R., and Brand, L. (1979). Analysis of two-state excited-state reactions. The fluorescence decay of 2-naphthol, *J. Physiol. Chem.* 83:795-802.
35. Gafni, A., and Brand, L. (1978). Excited state proton transfer reactions of acridine studied by nanosecond fluorometry, *Chem. Phys. Letts.* 58:346-350.
36. Lakowicz, J. R. and Balter, A. (1982a). Theory of phase-modulation fluorescence spectroscopy for excited state processes, *Biophys. Chem.* 16:99-115.
37. Lakowicz, J. R., and Balter, A. (1982). Analysis of excited state process by phase-modulation fluorescence spectroscopy, *Biophys. Chem.* 16:117-132.
38. Cheung, H. C. (1991). Resonance energy transfer in *Topics in Fluorescence Spectroscopy, Vol: 2 Principles*, (J. R. Lakowicz, Ed.), Plenum Press, New York, pp. 127-176.
39. Clegg, R. M. (1992). Fluorescence resonance energy transfer and nucleic helical geometry of double-stranded DNA in solution by fluorescence resonance energy transfer, *Proc. Natl. Acad. Sci.* 211:353-388.
40. Clegg, R. M., Murchie, A. I., Zechel, A., and Lilley, D. M. (1993). Observing the helical geometry of double-stranded DNA in solution by fluorescence resonance energy transfer, *Proc. Natl. Acad. Sci. USA* 90:2994-2998.
41. Root, D. D. (1997). In situ molecular association of dystrophin with actin revealed by sensitized emission immuno-resonance energy transfer, *Proc. Natl. Acad. Sci.* 94:5685-5690.
42.
43. Selvin, P. R. (1996). Lanthanide-based resonance energy transfer, *IEEE J. Selected Topics in Quantum Electronics* 2(4): 1077-1087.
44. Chen, J., and Selvin, P. R. (2000). Lifetime- and color-tailored fluorophores in the micro- and millisecond time regime, *J. Am. Chem. Soc.* 122:657-660.
45. Selvin, P. R., and Hearst, J. E. (1994). Luminescence energy transfer using a terbium chelate: Improvements on fluorescence energy transfer, *Proc. Natl. Acad. Sci. U.S.A.* 91:10024-10028.
46. Benson, S. C., Mathies, R. A., and Glazer, A. N. (1993). Heterodimeric DNA-binding dyes designed for energy transfer. Stability and application of the DNA complexes, *Nucleic Acids* 21:5720-5726.
47. Benson, S. C., Zeng, Z., and Glazer, A. N. (1995). Fluorescence energy-transfer cyanine heterodimers with high affinity for double-stranded DNA, *Anal. Biochem.* 231: 247-255.
48. Klakamp, S. L., and DeW. Horrocks, W. (1992). Lanthanide ion luminescence as a probe of DNA structure. 1. Guanine-containing oligomers and nucleotides, *J. Inorg. Biochem.* 46:175-192.
49. Klakamp, S. L., and DeW. Horrocks, W. (1992). Lanthanide ion luminescence as a probe of DNA structure. 2. Non-guanine containing oligomers and nucleotides, *J. Inorg. Biochem.* 46:193-205.

50. Fu, P. K. L., and Turro, C. (1999). Energy transfer from nucleic acids to Tb(III): Selective emission enhancement by single DNA mismatches, *J. Am. Chem. Soc.* 121(1):1-7.
51. Malak H., Gryczynski I., Lakowicz J. R., Meyers G. J. and Castellano F. N. (1997) Long-lifetime metal-ligand complexes as luminescent probes for DNA. *Journal of Fluorescence* 7(2): 107-112.
52. Lakowicz J. R., Malak H., Gryczynski I., Castellano F. N. and Meyer G. J. (1995) DNA dynamics observed with long lifetime metal-ligand complexes. *Biospectroscopy* 1:163-168.
53. Stryer, L., and Haugland, R. P. (1967). Energy transfer: A spectroscopic ruler, *Proc. Natl. Acad. Sci.* 58:719-726.
54. Parkhurst, K. M., and Parkhurst, L. J. (1996). Detection of point mutations in DNA by fluorescence energy transfer, *J. Biomed. Optics* 1:435-441.
55. Hochstrasser, R. A., and Chen, S. M., and Millar, D. P. (1992). Distance distribution in a dye-linked oligonucleotide determined by time-resolved fluorescence energy transfer, *Biophys. Chem.* 45:133-141.
56. Harriman, A., Hissler, M., Khatyr, A., and Ziessel, R. (1999). A ruthenium(II) tris-(2,2'-bipyridine) derivative possessing a triplet lifetime of 42 μs, *Chem. Commun.* 735-736.
57. Simon, J. A., Curry, S. L., Schmehl, R. H., Schatz, T. R., Piotrowiak, P., Jin, X., and Thummel, R. P. (1997). Intramolecular electron energy transfer in ruthenium (II) diimine donor/pyrene acceptor complexes linked by a single C—C bond, *J. Am. Chem. Soc.* 119:11012-11022.
58. Morrison, L. E. (1995). Detection of energy transfer and fluorescence quenching, in *Nonisotopic Probing, Blotting, and Sequencing*, L. J. Kricka (Ed.), Academic Press, New York, pp. 429-471.
59. Parkhurst, K. M., and Parkhurst, L. J. (1996). Detection of point mutations in DNA by fluorescence energy transfer, *J. Biomed. Opt.* 1:435-441.
60. Ota, N., Hirano, K., Warashina, M., Andrus, A., Mullah, B., Hatanaka, K., and Taira, K. (1998). Determination of interactions between structured nucleic acids by fluorescence resonance energy transfer (FRET): Selection of target sites for functional nucleic acids, *Nucleic Acids Res.* 26(3):735-743.
61. Kostrikis, L., Tyagi, S., Mhlanga, M. M., Ho, D. D., and Kramer, F. R. (1998). Spectral genotyping of human alleles, *Science* 279:1228-1229.
62. Tyagi, S., Bratu, D. P., and Kramer, F. R. (1998). Multicolor molecular beacons discrimination, *Nature Biotechnology* 16:49-52.
63. Steemers, F. J., Ferguson, J. A., and Walt, D. R. (2000). Screening unlabeled DNA targets with randomly ordered fiber-optic gene arrays, *Nature Biotechnology* 18:91-94.
64. Brown, P. O., and Botstein, D. (1999). Exploring the new world of the genome with DNA microarrays, *Nature Genetics Suppl.* 21:33-37.
65. Cheung, V. G., Morley, M., Aguilar, F., Massimi, A., Kucherlapati, R., and Childs, G. (1999). Making and reading microarrays, *Nature Genet Suppl.* 21:15-19.
66. Hacia, J. G., Brody, L. C., and Collins, F. S. (1998). Applications of DNA chips for genomic analysis, *Molecular Psychiatry* 3:483-492.
67. Harrington, C. A., Rosenow, C., and Retief, J. (2000). Monitoring gene expression using DNA microarrays, *Curr. Opin. Microbiol.* 3:285-291.
68. Abramowitz, S. (1999). DNA analysis in microfabricated formats, *J. Biomed. Microdevices* 1: 107-112.
69. Walter, N. G., Burke, J. M., and Millar, D. P. (1999). Stability of hairpin ribozyme tertiary structure is goverend by the interdomain junction, *Nature Structural Biology* 6(6):544-549.
70. Walter, N. G., Hampel, K. J., Brown, K. M., and Burke, J. M. (1998). Tertiary structure formation in the hairpin ribozyme monitored by fluorescence resonance energy transfer, *The EMBO Journal* 17(8):2378-2391.
71. Czarnik, A. W. (Ed.) (1993). *Fluorescent Chemosensors for Ion and Molecule Recognition*, American Chemical Society, Waashington, D.C.
72. Lakowicz, J. R. (Ed.) (1994). *Topics in Fluorescence Spectroscopy, Volume 4: Probe Design and Chemical Sensing*, Plenum Press, New York, pp. 501.
73. Pope, A. J., Haupts, U. M., and Moore, K. J. (1999). Homogeneous fluorescence readouts for miniaturized high-throughput screening: theory and practice, *DDT* 4(8): 350-362.
74. Mere, L., Bennett, T., Coassin, P., England, P., Hamman, B., Rink, T., Zimmerman, S., and Negulescu, P. (1999). Miniaturized FRET assays and microfluidics: key components for ultra-high-throughput screening, *DDT* 4(8):363-367.
75. Lakowicz, J. R. and Maliwal, B. P. (1985) Construction and performance of a variable-frequency phase-modulation fluorometer. *Biophys. Chem.* 21:61-78.
76. Feddersen B. A., Piston D. W. and Gratton E. (1989) Digital parallel acquisition in frequency domain fluorimetry, *Rev. Sci. Instrum.* 60(9):2929-2936.
77. Netzel, T. L., Nafisi, K., Zhao, M., Lenhard, J. R., and Johnson, I. (1995). Base-content dependence of emission enhancements, quantum yields, and lifetimes for cyanine dyes to double-strand DNA: Photophysical properties of monomeric and bichromophoric DNA stains, *J. Phys. Chem.* 99:17936-17947.
78. Haugen, G. R., Wallin, B. W., and Lytle, F. E. (1979). Optimization of data-acquisition rates in time-correlated single-photon fluorimetry, *Rev. Sci. Instrum.* 50:64-72.
79. Barisas, B. G., and Lauther, M. D. (1980). Grid-gated photomultiplier photometer with subnanosecond time response, *Rev. Sci. Instrum.* 51:74-78.
80. James, D. R., Siemiarczuk, A., and Ware, W. R. (1992). Stroboscopic optical boxcar technique for the determination of fluorescence lifetimes, *Rev. Sci. Instrum.* 63:1710-1716.
81. Lovgren, T., Hemmila, I., Pettersson, K., and Halonen, P. (1985). Time-resolved fluorescence fluorometry in immunoassays, in *Alternative Immunoassays*, (W. P. Collins, Ed.), John Wiley & Sons, New York, pp. 203-217.
82. Diamandis, E. P. (1988). Immunoassays with time-resolved fluorescence spectroscopy: Principles and applications, *Clin. Biochem.* 21:139-150.

The invention claimed is:

1. A luminophore comprising a donor portion (D) in close association with an acceptor portion (A) sufficient for resonant energy transfer therebetween, wherein upon excitation by external electromagnetic radiation of a wavelength shorter than $\lambda_1$, said luminophore emits luminophore radiation in the range of about 450 to about 1200 nm of a wavelength longer than $\lambda_1$, with an emission lifetime $t_1$ and a quantum yield $Q_1$,
    wherein when D is not in said close association with A, it absorbs radiation of a wavelength $\lambda_2$ shorter than $\lambda_1$ and thereafter emits radiation with a quantum yield $Q_2$ less than about 0.2,
    wherein when said donor portion is in said close association with A and is excited by electromagnetic radiation of wavelength shorter than $\lambda_1$, it resonantly transfers energy to said acceptor portion A which then resonantly emits radiation of a wavelength longer than $\lambda_1$ with said emission lifetime $t_1$ and quantum yield $Q_1$, which is substantially greater than $Q_2$,
wherein said luminophore is a chemical compound, wherein D is covalently linked to A, and has the formula:
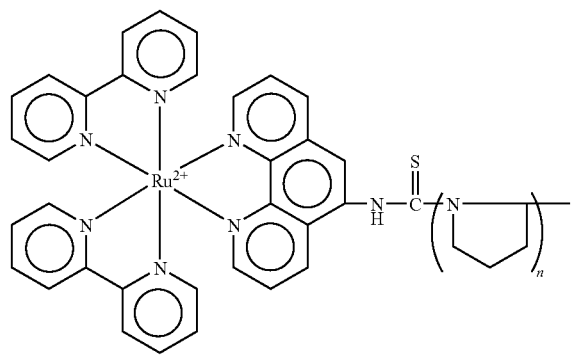
wherein $C_5X =$
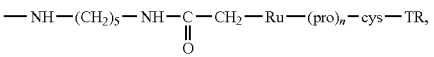
$n = 6$ or $8$, and TR = Texas Red.
* * * * *